US006407064B2

(12) United States Patent
Masuda et al.

(10) Patent No.: US 6,407,064 B2
(45) Date of Patent: Jun. 18, 2002

(54) AMINOALCOHOL DERIVATIVE AND MEDICAMENT COMPRISING THE SAME

(75) Inventors: Hiroyuki Masuda; Masayuki Jinbo, both of Tokyo (JP); Keiichiro Sakai, Ontario (CA); Yuji Matsuzaki, Saitama (JP)

(73) Assignee: Seikagaku Corporation, Tokyo (JP)

( * ) Notice: Subject to any disclaimer, the term of this patent is extended or adjusted under 35 U.S.C. 154(b) by 0 days.

(21) Appl. No.: 09/729,266

(22) Filed: Dec. 5, 2000

(30) Foreign Application Priority Data

Dec. 6, 1999 (JP) .......................... 11-346526

(51) Int. Cl.[7] ............... A61K 31/535; A61K 31/70; A61K 38/00; C07D 295/088; C07D 295/13
(52) U.S. Cl. ............. 514/18; 514/19; 514/25; 514/35; 514/43; 514/237.8; 530/331; 536/17.4; 536/29.11; 544/168; 544/169

(58) Field of Search .............. 514/18, 19, 25, 514/35, 43, 237.8; 530/331; 536/17.4, 29.11; 544/168, 169

(56) References Cited

U.S. PATENT DOCUMENTS 5,763,438 A * 6/1998 Inokuchi et al. ......... 514/237.8
6,040,332 A * 3/2000 Shayman et al. ........... 514/428
6,335,444 B1 * 1/2002 Jinbo et al. ................ 544/168

FOREIGN PATENT DOCUMENTS

EP 0 720 852 7/1996

* cited by examiner

*Primary Examiner*—Jeffrey E. Russel
(74) *Attorney, Agent, or Firm*—Oblon, Spivak, McClelland, Maier & Neustadt, P.C.

(57) ABSTRACT

An aminoalcohol derivative which is a ceramide analogue, and a medicament, especially an agent for treating neuronal diseases and an agent for protecting brain, comprising the same.

15 Claims, No Drawings

AMINOALCOHOL DERIVATIVE AND MEDICAMENT COMPRISING THE SAME

BACKGROUND OF THE INVENTION

1. Field of the Invention

The present invention relates to an aminoalcohol derivative which is a ceramide analogue and a medicament, particularly an agent for treating neuronal diseases and an agent for protecting brain, comprising the same.

2. Brief Description of the Background Art

Glycosphingolipids (hereinafter referred to as "GSL") are present as a constitutional component of cell surface membranes of mammalian cells and play important roles in cellular functions, such as development, growth, differentiation, malignant transformation, immunoreaction and the like, through a receptor function of a physiologically active substance, an intercellular mutual recognizing function, an intercellular interaction, and the like.

Among them, a ganglioside is a GSL containing sialic acid and is said to be active in the recovery from neuronal diseases, such as peripheral nervous injury, central nervous disorder and the like, i.e., an acceleration of nervous regeneration and a process of neurotransmission. Heretofore, the effectiveness of exogenous gangliosides has been investigated toward various pathological models of nervous system. As a medicament utilizing the same, a medicament named "Cronassial™" has already been commercialized in Italy and a related patent is also known (JP-B-62-50450).

Currently, the addition of a ganglioside to an experimental system from outside is the most popular type of a procedure for searching a function of the ganglioside. In that case, however, a relation to endogenous gangliosides becomes a problem. That is, it is considered that the result obtained from the further addition of the ganglioside to the system where endogenous gangliosides present in cell membranes have already formed complexes with various cell surface receptors etc. does not always reflect the actual cytophysiological significance of endogenous gangliosides. Therefore, a method of specifically changing biosynthesis of endogenous GSLs is necessary to identify an intrinsic role of a ganglioside in cell cytophysiology.

Incidentally, it is reported that a ceramide analogue, D-threo-1-phenyl-2-decanoylamino-3-morpholino-1-propanol (D-threo-PDMP) specifically inhibits an enzyme for glucosylceramide biosynthesis and remarkably reduces intracellular content of all GSLs which are produced starting with glucosylceramide (*J. Lipid Res.*, 28: 565–571 (1987)). Furthermore, it is also reported that D-threo-PDMP suppresses the extension of neurite (*J. Biochem.*, 110: 96–103 (1991)). In addition, it has been found that D-threo-PDMP suppresses synaptic function and the suppression is specifically released by GQ1b among various gangliosides (*Biochem. Biophys. Res. Commun.*, 222: 494–498 (1996)). Based on these results, it is suggested that the ganglioside GQ1b is an active molecule necessary for synaptic function and the importance of endogangliosides on nervous functions is recognized.

On the other hand, there is suggested a possibility that L-threo-PDMP (hereinafter often referred to as "L-PDMP") which is an optical enantiomer of D-threo-PDMP accelerates the biosynthesis of GSL (*J. Cell. Physiol.*, 141: 573–583 (1989)).

In addition, it is also shown that 2-acylaminopropanol compounds, such as L-threo-PDMP and the like, accelerate ganglioside biosynthesis of neurocytes and exhibit an effect of accelerating neurite extension (*J. Neurochem.*, 67: 1821–1830, 1996) and an effect of accelerating synapse formation, and therefore, is promising as an agent for treating neuronal diseases (WO 95/05177).

Furthermore, as a result of the examination of the effects of L-threo-PDMP on MAPkinase (mitogen-activated protein kinase) activated when synaptic transmission is continuously accelerated by N-methyl-D-aspartate (NMDA) or a brain derived neurotropic factor (BDNF) in order to elucidate an action mechanism of the neurotropic factor-like activity of L-threo-PDMP, it was found that L-threo-PDMP activates MAPkinase for a long period of time in proportion to the effect of accelerating synapse formation and further, L-threo-PDMP increases the activity of an enzyme for GQ1b synthesis (*Biochem. Biophys. Res. Commun.*, 237: 595–600 (1997)).

However, in order to exhibit the pharmaceutical effect of L-threo-PDMP in vivo, it is judged that there is room for the improvement in an pharmaceutical effect-toxicity ratio and a distribution ability of the compound into tissues.

SUMMARY OF THE INVENTION

An object of the present invention is to provide an aminoalcohol derivative or pharmaceutically acceptable salt thereof which has an activity of accelerating synapse formation and/or an activity of accelerating glycolipid biosynthesis, a low toxicity, and an improved distribution ability into tissues.

Another object of the present invention is to provide a medicament, particularly an agent for treating neuronal diseases or an agent for protecting brain comprising the aminoalcohol derivative.

The present invention have been achieved by an aminoalcohol derivative which is a ceramide analogue, and a medicament, especially an agent for treating neuronal diseases and an agent for protecting brain, comprising the same.

A first embodiment of the present invention is as follows:

(1) An aminoalcohol derivative represented by formula (I):

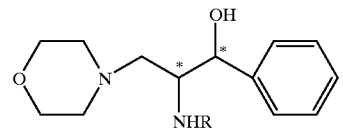

(I)

wherein * represents an asymmetric carbon; and

R represents a residue of a monocarboxylic acid derivative represented by the following (i) or (ii), or a residue of a dicarboxylic acid or a derivative thereof represented by the following (iii):

(i) a residue of glycine or polyglycine represented by $(COCH_2NH)_mZ$, wherein m represents an integer of from 1 to 3; and Z represents an amino-protecting group or an alkanoyl group;

(ii) a residue of a carboxylic acid derivative represented by CO—W—Y, wherein W represents an alkylene group or a cycloalkylene group; and Y represents a hydroxyl group, a monosaccharide residue, an aryl group which is optionally substituted, or an alkoxyl group optionally having an oxygen atom in the alkyl chain;

(iii) a residue of a dicarboxylic acid or a derivative thereof represented by CO—W—CO—X,
wherein W represents an alkylene group or a cycloalkylene group; and
X represents a hydroxyl group, a chain or cyclic alkoxyl group, an alkyl group, an α-amino acid residue, or $NR^1R^2$, in which $R^1$ and $R^2$ are the same or different and each independently represents a hydrogen atom, a chain or cyclic alkyl group optionally having an oxygen atom in the alkyl chain, or a chain or cyclic hydroxyalkyl group optionally having an oxygen atom in the alkyl chain, or
a pharmaceutically acceptable salt thereof.

A second embodiment of the present invention is as follows:

(2) A medicament comprising, as an active ingredient, the aminoalcohol derivative represented by formula (I) or a pharmaceutically acceptable salt thereof.

Also, the compound of formula (I) has 4 configurations, (1S,2S), (1S,2R), (1R,2S), and (1R,2R). As the active ingredient of an agent for treating neuronal diseases and an agent for protecting brain, L-threo compound having a configuration of (1S,2S) is preferred.

Specific embodiments of the present invention include the following aminoalcohol derivatives and pharmaceutically acceptable salts thereof:

(a) The aminoalcohol derivative according to the above (1), wherein R is represented by any one of the following (i) to (iii) in formula (I):
(i) $(COCH_2NH)_mZ$,
wherein Z represents an amino-protecting group selected from an aralkyloxycarbonyl group having from 8 to 15 carbon atoms and an alkoxycarbonyl group having from 5 to 7 carbon atoms, or an alkanoyl group having from 4 to 8 carbon atoms;
(ii) CO—W—Y,
wherein W represents an alkylene group having from 1 to 12 carbon atoms or a cycloalkylene group having from 4 to 8 carbon atoms; and
Y represents a hydroxyl group, a glucose residue, a galactose residue, an N-acetylglucosamine residue, an N-acetylgalactosamine residue, a mannose residue, a fucose residue, a sialic acid residue, a phenyl group which is optionally substituted, an alkoxyl group having from 1 to 6 carbon atoms, or an alkoxyl group having from 4 to 12 carbon atoms having from 1 to 3 oxygen atoms in the alkyl chain;
CO—W—CO—X,
wherein W represents an alkylene group having from 1 to 12 carbon atoms or a cycloalkylene group having from 4 to 8 carbon atoms; and
X represents a hydroxyl group, an alkoxyl group having from 1 to 8 carbon atoms, a cycloalkoxyl group having from 5 to 8 carbon atoms, an alkyl group having from 1 to 6 carbon atoms, a residue of an α-amino acid having a reactive functional group in the side chain, or $NR^1R^2$, in which $R^1$ and $R^2$ are the same or different and each independently represents a hydrogen atom, an alkyl group having from 1 to 6 carbon atoms, cyclohexyl group or a hydroxyalkyl group having from 2 to 4 carbon atoms, or
a pharmaceutically acceptable salt thereof.

(b) The aminoalcohol derivative according to the above (1), wherein R is represented by any one of the following (i) to (iii) in formula (I):

(i) $(COCH_2NH)_mZ$,
wherein Z represents a benzyloxycarbonyl group, a t-butoxycarbonyl group, or a hexanoyl group;
(ii) CO—W—Y,
wherein W represents an alkylene group having from 1 to 9 carbon atoms; and
Y represents a hydroxyl group, a glucose residue, a galactose residue, an N-acetylglucosamine residue, an N-acetylgalactosamine residue, a sialic acid residue, a phenyl group which is substituted with an alkoxyl group having from 1 to 3 carbon atoms, an alkoxyl group having from 1 to 4 carbon atoms, or an alkoxyl group having from 6 to 8 carbon atoms having an oxygen atom in the alkyl chain;
(iii) CO—W—CO—X,
wherein W represents an alkylene group having from 2 to 8 carbon atoms or a cyclohexylene group; and
X represents a hydroxyl group, an alkoxyl group having from 1 to 4 carbon atoms, a cyclohexyloxy group, a methyl group, a residue of an amino acid selected from lysine, arginine, histidine, aspartic acid, glutamic acid, ornithine, cysteine, serine, threonine and tyrosine, or $NR^1R^2$, in which $R^1$ and $R^2$ are the same or different and each independently represents a hydrogen atom, a straight chain alkyl group having from 1 to 6 carbon atoms, a cyclohexyl group, or a hydroxyethyl group, or
a pharmaceutically acceptable salt thereof.

(c) The aminoalcohol derivative according to the above (1), wherein, in formula (I), R is represented by CO—W—CO—X, in which W represents an alkylene group having from 2 to 8 carbon atoms; and X represents a hydroxyl group, an alkoxyl group having from 1 to 4 carbon atoms, or a methyl group, or a pharmaceutically acceptable salt thereof.

(d) The aminoalcohol derivative according to the above (1), wherein, in formula (I), R is represented by CO—W—CO—X, in which W represents an alkylene group having from 4 to 8 carbon atoms; and X represents a lysine residue or an ornithine residue, or a pharmaceutically acceptable salt thereof.

(e) The aminoalcohol derivative according to the above (1), wherein, in formula (I), R is represented by CO—W—CO—X, in which W represents an alkylene group having from 4 to 8 carbon atoms or cyclohexylene group; and X represents $NR^1R^2$, in which $R^1$ and $R^2$ are the same or different and each independently represents a hydrogen atom, a methyl group, an ethyl group, a propyl group, an n-butyl group, an n-hexyl group, a cyclohexyl group, or a hydroxyethyl group, or a pharmaceutically acceptable salt thereof.

(f) The aminoalcohol derivative according to the above (1), wherein, in formula (I), R is represented by CO—W—Y, in which W represents a nonylene group; and Y represents a hydroxyl group, or a pharmaceutically acceptable salt thereof.

(g) The aminoalcohol derivative according to the above (1), wherein, in formula (I), R is represented by CO—W—Y, in which W represents a methylene group; and Y represents an n-butoxy group or an alkoxyl group having from 6 to 8 carbon atoms having an oxygen atom in the alkyl chain, or a pharmaceutically acceptable salt thereof.

(h) The aminoalcohol derivative according to the above (1), wherein, in formula (I), R is represented by CO—W—Y, in which W represents an octylene group; and Y represents a sialic acid residue, or a pharmaceutically acceptable salt thereof.

Furthermore, embodiments of suitable medicaments of the present invention include an agent for treating neuronal diseases and an agent for protecting brain, comprising, as an active ingredient, the aminoalcohol derivative described in any one of the above (1) and (a) to (h) or a pharmaceutically acceptable salt thereof.

DETAILED DESCRIPTION OF THE INVENTION

The present inventors have found that the modification of an acylamino group of a 2-acylaminopropanol compound, such as L-threo-PDMP or the like, lowers the toxicity of the compound and remarkably improves a distribution ability of the compound into tissues when the compound is administered to a mammal, and have accomplished the present invention based on these findings.

The compound of the present invention is an aminoalcohol derivative represented by formula (I) or a pharmaceutically acceptable salt thereof (hereinafter often referred to as "the compound of the present invention"), and the definitions (i) to (iii) of substituent R in the formula are as described above. Specific examples corresponding to the definitions (i) to (iii) are shown below.

Examples of the compound of the present invention represented by formula (I) wherein R is $(COCH_2NH)_m Z$ include aminoalcohol derivatives, wherein m represents an integer of from 1 to 3, preferably 1 or 2; and Z represents an amino-protecting group selected from an aralkyloxycarbonyl group having from 8 to 15 carbon atoms and an alkoxycarbonyl group having from 5 to 7 carbon atoms, or an alkanoyl group having from 4 to 8 carbon atoms, or pharmaceutically acceptable salts thereof.

The amino-protecting group includes urethane-type protecting groups. Examples include a benzyloxycarbonyl group, a p-nitrobenzyloxycarbonyl group, a p-bromobenzyloxycarbonyl group, a p-methoxybenzyloxycarbonyl group, a p-methoxyphenylazobenzyloxycarbonyl group, a p-phenylazobenzyloxycarbonyl group, a t-butoxycarbonyl group, and a cyclopentyloxycarbonyl group. Among these, a benzyloxycarbonyl group and a t-butoxycarbonyl group are preferred. The alkanoyl group is preferably a hexanoyl group.

Specific examples of the compounds represented by formula (I) wherein R is $(COCH_2NH)_m Z$ include:

(1S,2S)-2-benzyloxycarbonylglycylamino-3-morpholino-1-phenyl-1-propanol,
(1S,2S)-2-benzyloxycarbonylglycylglycylamino-3-morpholino-1-phenyl-1-propanol,
(1S,2S)-2-(n-butoxy)carbonylglycylamino-3-morpholino-1-phenyl-1-propanol, and
(1S,2S)-2-(n-hexanoyl)glycylamino-3-morpholino-1-phenyl-1-propanol.

Examples of the compound of the present invention represented by formula (I) wherein R is CO—W—CO—X include aminoalcohol derivatives, wherein W represents an alkylene group having from 1 to 12 carbon atoms or a cycloalkylene group having from 4 to 8 carbon atoms; and X represents a hydroxyl group, an alkoxyl group having from 1 to 8 carbon atoms, a cycloalkoxyl group having from 5 to 8 carbon atoms, an alkyl group having from 1 to 6 carbon atoms, a residue of an α-amino acid having a reactive functional group (e.g., amino group, guanidino group, carboxyl group, or hydroxyl group) in the side chain, or $NR^1R^2$ (in which $R^1$ and $R^2$ are the same or different and each independently represents a hydrogen atom, an alkyl group having from 1 to 6 carbon atoms, a cyclohexyl group, or a hydroxyalkyl group having from 2 to 4 carbon atoms), or pharmaceutically acceptable salts thereof. Specific examples include compounds, wherein W represents an alkylene group having from 2 to 8 carbon atoms or a cyclohexylene group; and X represents a hydroxyl group, an alkoxyl group having from 1 to 4 carbon atoms, a cyclohexyloxy group; methyl group, a residue of an α-amino acid selected from lysine, arginine, histidine, aspartic acid, glutamic acid, ornithine, cysteine, serine, threonine and tyrosine, or $NR^1R^2$ (in which $R^1$ and $R^2$ are the same or different and each independently represents a hydrogen atom, a straight chain alkyl group having from 1 to 6 carbon atoms, a cyclohexyl group, or a hydroxyethyl group).

More specific examples of the compound represented by formula (I) wherein R is CO—W—CO—X include:

(1S,2S)-2-(n-butoxy)butanedioylamino-3-morpholino-1-phenyl-1-propanol,
(1S,2S)-2-ethoxyhexanedioylamino-3-morpholino-1-phenyl-1-propanol,
(1S,2S)-2-isopropoxyhexanedioylamino-3-morpholino-1-phenyl-1-propanol,
(1S,2S)-2-(n-butoxyhexanedioyl)amino-3-morpholino-1-phenyl-1-propanol,
(1S,2S)-2-methoxydecanedioylamino-3-morpholino-1-phenyl-1-propanol,
(1S,2S)-2-(9-carboxynonanoyl)amino-3-morpholino-1-phenyl-1-propanol,
(1S,2S)-2-(7-oxooctanoyl)amino-3-morpholino-1-phenyl-1-propanol,
(1S,2S,12S)-2-(12-amino-7-aza-6-oxo-12-carboxydodecanoyl)amino-3-morpholino-1-phenyl-1-propanol, and
(1S,2S,16S)-2-(16-amino-11-aza-10-oxo-16-carboxyhexadecanoyl)amino-3-morpholino-1-phenyl-1-propanol.

In addition, examples also include:

(1S,2S)-2-(3-butylcarbamoyl)propionylamino-3-morpholino-1-phenyl-1-propanol,
(1S,2S)-2-(N-butyl-N-methylamino)butanedioylamino-3-morpholino-1-phenyl-1-propanol,
(1S,2S)-2-(5-ethylcarbamoyl)pentanoylamino-3-morpholino-1-phenyl-1-propanol,
(1S,2S)-2-(5-cyclohexylcarbamoyl)pentanoylamino-3-morpholino-1-phenyl-1-propanol,
(1S,2S)-2-(5-hexylcarbamoyl)pentanoylamino-3-morpholino-1-phenyl-1-propanol,
(1S,2S)-2-(9-butylcarbamoyl)nonanoylamino-3-morpholino-1-phenyl-1-propanol,
(1S,2S)-2-(9-hexylcarbamoyl)nonanoylamino-3-morpholino-1-phenyl-1-propanol,
(1S,2S)-2-(N,N-diethanolamino)decanedioylamino-3-morpholino-1-phenyl-1-propanol, and
(1S,2S)-2-(cyclohexane-4-hexylcarbamoyl-1-carbonyl)amino-3-morpholino-1-phenyl-1-propanol.

Furthermore, examples of the compound of the present invention wherein R is CO—W—Y in formula (I) include aminoalcohol derivatives, wherein W represents an alkylene group having from 1 to 12 carbon atoms or a cycloalkylene group having from 4 to 8 carbon atoms; and Y represents a hydroxyl group, a glucose residue, a galactose residue, an N-acetylglucosamine residue, an N-acetylgalactosamine residue, a mannose residue, a fucose residue, a sialic acid residue, a phenyl group which is optionally substituted, an alkoxyl group having from 1 to 6 carbon atoms, or an alkoxyl group having from 4 to 12 carbon atoms having from 1 to 3 oxygen atoms in the alkyl chain, or a pharmaceutically acceptable salt thereof. Specific examples include compounds, wherein W represents an alkylene group having from 1 to 9 carbon atoms; and Y represents a hydroxyl group, a glucose residue, a galactose residue, an N-acetylglucosamine residue, an N-acetylgalactosamine residue, a sialic acid residue, a phenyl group which is substituted with an alkoxyl group having from 1 to 3 carbon atoms, an alkoxyl group having from 1 to 4 carbon atoms or an alkoxyl group having from 6 to 8 carbon atoms having an oxygen atom in the alkyl chain.

More specific examples of the compound represented by formula (I) wherein R is CO—W—Y include:

(1S,2S)-2-(10-hydroxydecanoyl)amino-3-morpholino-1-phenyl-1-propanol,
(1S,2S)-2-(9-sialylnonanoyl)amino-3-morpholino-1-phenyl-1-propanol,
(1S,2S)-2-[4-(4-methoxyphenyl)butyryl]amino-3-morpholino-1-phenyl-1-propanol,
(1S,2S)-2-(3-oxaheptanoyl)amino-3-morpholino-1-phenyl-1-propanol,
(1S,2S)-2-(3,6-dioxadecanoyl)amino-3-morpholino-1-phenyl-1-propanol, and
(1S,2S)-2-(3,6-dioxadodecanoyl)amino-3-morpholino-1-phenyl-1-propanol.

Among the compounds of the present invention, the particular examples of the compounds having a low toxicity and a high activity of synapse formation are especially the compounds wherein R is represented by CO—W—CO—X or the compounds wherein R is represented by CO—W—Y, in which W and X or Y are represented by the following combinations shown in Table 1.

TABLE 1

| W | X | Y | No.* |
|---|---|---|---|
| Ethylene group | Butoxy group | | 5 |
| Butylene group | Lysine residue | | 26 |
| Octylene group | Lysine residue | | 27 |
| Butylene group | Ethylamino group | | 11 |
| Octylene group | Butylamino group | | 14 |
| Nonylene group | | Hydroxyl group | 23 |
| Octylene group | | Sialic acid residue | 28 |
| Methylene group | | Butoxyethyleneoxy group | 19 |
| Methylene group | | Hexyloxyethyleneoxy group | 21 |

*No.: Compound No. (corresponding to Example No. described below)

The aminoalcohol derivative of the present invention is obtained by introducing the substituent R to an amino group of an aminoalcohol derivative represented by formula (II) through a peptide bond-forming reaction which itself is already known in the art using a carboxylic acid corresponding to R or its reactive derivative, but the preparation of the compounds is not limited to such a method.

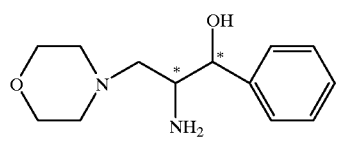

(II)

When the carboxylic acid compound corresponding to R contains a highly reactive functional group, the functional group can be protected with an appropriate protecting group in advance and, after a desired peptide bond-forming reaction, the protecting group can be removed. Furthermore, the desired compound can be obtained by subjecting repeatedly the reactive functional group (e.g., amino group or carboxyl group) to a peptide bond-forming reaction or esterifying reaction which itself is already known in the art.

Examples of the peptide bond-forming method include a method using a carboxylic acid corresponding to the above R and a condensing agent, a method using an acid anhydride, and a method using an acid halide.

Specifically, examples include a method of reacting an aminoalcohol derivative represented by formula (II) or acid adduct salt thereof (e.g., hydrochloride) with the carboxylic acid and a condensing agent (e.g., dicyclohexylcarbodiimide (DCC) or water soluble carbodiimide (WSC), more specifically 1-ethyl-3-(3-dimethylaminopropyl)carbodiimide hydrochloride (EDC)) in a solvent such as water, methylene chloride, pyridine or ethanol using, if necessary, an activating agent such as N-hydroxysuccinimide; and a method of reacting the same using an acid anhydride or acid halide (e.g., acid chloride) and a base (e.g., an organic base such as pyridine, triethylamine, diisopropylethylamine or N-methylmorpholine, or an inorganic base such as sodium hydrogen carbonate). The solvent to be used in the reaction is not particularly limited unless it inhibits the peptide bond-forming reaction provided that it dissolves the aminoalcohol derivative and the carboxylic acid compound.

The peptide bond-forming reaction is carried out usually at about 0 to 50° C., preferably at room temperature (5 to 35° C. (JIS K0050)) for several hours to several days, preferably 10 hours to 2 days, but the reaction conditions can be suitably determined by those skilled in the art through a preliminary experiment.

After the peptide bond-forming reaction, the compound of the present invention represented by formula (I) can be purified and isolated by suitably combining purifying means which themselves are known, for example, an extraction with a solvent, such as ethyl acetate, chloroform or the like, various types of chromatography (adsorption chromatography, ion exchange chromatography, etc.), and crystallization.

As the method for producing the compound of formula (II) which is a starting material for the compound of the present invention, the known method described in JP-A-9-216856 can be optionally adopted. Concretely, the compound is obtained as the compound having a desired stereochemical configuration through successive reaction according to the reaction scheme shown in the following by use of a chiral compound represented by formula (III) as the starting material.

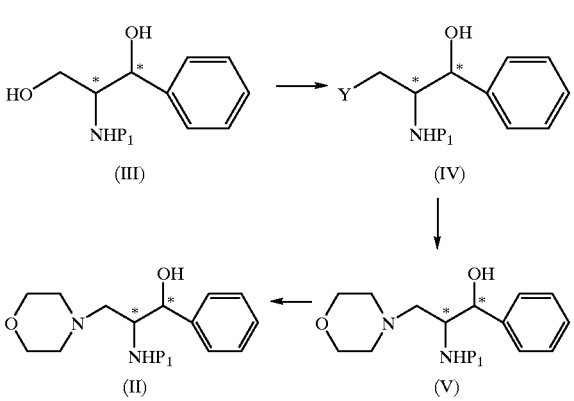

wherein * represents an asymmetric carbon; $P_1$ represents an amino-protecting group (e.g., benzyloxycarbonyl group, t-butoxycarbonyl group, benzenesulfonyl group, or fluorenylmethoxycarbonyl group); and Y represents a leaving group (e.g., methanesulfonyl group, trihalogenomethanesulfonyl group, p-toluenesulfonyl group, benzenesulfonyl group, or p-bromobenzenesulfonyl group)

Namely, a leaving group (Y) is introduced only to the primary hydroxyl group of the aminoalcohol derivative represented by formula (III) to form a compound represented by formula (IV) and then, the resulting compound is reacted with morpholine to form an aminoalcohol derivative represented by formula (V). A chiral aminoalcohol derivative represented by formula (II) is finally obtainable by removing $P_1$ from the compound.

The compound of formula (II) thus obtained is converted into the compound of formula (I) according to the above-described reaction.

The pharmaceutically acceptable salt of the compound of the present invention represented by formula (I) include salts with an inorganic acid, such as hydrochloric acid, phosphoric acid, sulfuric acid or nitric acid; and salts of an organic acid, such as formic acid, acetic acid, citric acid, lactic acid, malic acid, oxalic acid, maleic acid, fumaric acid, succinic acid, trifluoroacetic acid, methanesulfonic acid (mesylic acid), p-toluenesulfonic acid (tosylic acid) or the like. The salts can be produced according to an itself known method, and, for example, is produced by dissolving a compound (free-type) represented by formula (I) into a suitable solvent, such as alcohol or the like, adding usually equimolar amount of the above acid to react them, and then optionally evaporating the solvent.

The aminoalcohol derivative represented by formula (I) or pharmaceutically acceptable salt thereof which is the compound of the present invention has a property participating the action of controlling glycolipid biosynthesis and thus has utility as a medicament based on the property.

Among the compounds represented by formula (I), the compounds having an effect of accelerating synapse formation and/or an action of accelerating glycolipid (ganglioside etc.) biosynthesis are expected to have an effect of accelerating neurite extension, an effect of preventing neurocyte death, and an effect of activating MAPkinase, and therefore useful as an agent for treating neuronal diseases, based on such effects. Accordingly, by administering an effective amount of the compound of the present invention to mammals including human which suffer from neuronal diseases caused by disorders of peripheral nervous system or central nervous system, the animals can be treated. Examples of representative diseases include various diseases of central nervous system which are expected to be treated by regenerating nerve fibers, for example, stroke, cerebral infarction, sequelae of cerebrovascular accident, cerebral hemorrhage, cerebral injury, dysmnesia, senile dementia, Alzheimer's disease and Parkinson's disease; and various diseases of peripheral nervous system, for example, polyneuropathy caused by cacochymia, mechanical neuropathy and toxic neuropathy. In particular, the compound of the present invention having an activity of accelerating synapse formation is effective as an agent for treating diseases of central nervous system, particularly an agent for protecting brain or an agent for potentiating and protecting cerebral nerves, for example, for treating sequelae of cerebrovascular accident.

Formulation of Pharmaceutical Preparation

The compound of the present invention represented by formula (I) or pharmaceutically acceptable salt thereof can be used for treating various diseases (e.g., neuronal diseases) of mammals including human and a pharmaceutical preparation to be administered orally or parenterally can be obtained by using the compound or the salt with a carrier, an excipient, and other additives.

Examples of the oral preparation include solid preparations (e.g., powder, granule, capsule, tablet, etc.); and liquid preparations (e.g., syrup, elixir, emulsion, etc.). The powder can be obtained by, for example, mixing with an excipient, such as lactose, starch, crystalline cellulose, calcium lactate, calcium hydrogen phosphate, magnesium aluminometasilicate, silicic acid anhydride or the like. The granule can be obtained by adding the above excipient and, if necessary, for example, a binder, such as sucrose, hydroxypropyl cellulose, polyvinylpyrrolidone or the like, or a disintegrator, such as carboxymethyl cellulose, calcium carboxymethyl cellulose or the like, and granulating the mixture according to a wet method or a dry method. The tablet can be obtained by tableting the above powder or granule as such or with a lubricant, such as magnesium stearate, talc or the like. Furthermore, the above tablet or granule can be made an enteric or sustained action preparation by coating it with an enteric base, such as hydroxypropylmethyl cellulose phthalate, a methyl methacrylate copolymer, hydroxypropylmethyl cellulose acetate, hydroxypropylmethyl cellulose succinate or the like, or coating it with ethyl cellulose, carnauba wax, hardened oil, white shellac etc.

A hard capsule can be obtained by filling a hard capsule with the above powder or granule. Furthermore, a soft capsule can be obtained by dissolving the compound of the present invention in glycerin, polyethylene glycol, sesame oil, olive oil, etc. and covering the solution with a gelatin film.

The syrup can be obtained by dissolving a sweetener, such as sucrose, sorbitol, glycerin or the like, and the compound of the present invention in water. In addition to the sweetener and water, essential oil, ethanol and the like can be added to prepare an elixir, or gum arabic, tragacanth, a polysorbate (polysorbate 20, polysorbate 60, polysorbate 80 (Tween 80)), sodium carboxymethyl cellulose and the like can be added to prepare an emulsion or a suspension. Furthermore, a corrective, a coloring agent, a preservative and the like can be added to these liquid preparations, if necessary.

Examples of the parenteral preparation include injections, intrarectal preparations, pessary, endermic preparations, inhalants, aerosol, ophthalmic preparations, and the like. The injection can be obtained by adding a nonionic surfactant, such as a polysorbate or the like, if necessary; a pH-adjusting agent, such as hydrochloric acid, sodium hydroxide, lactic acid, sodium lactate, sodium monohydrogen phosphate, sodium dihydrogen phosphate or the like; an isotonizing agent, such as sodium chloride, glucose or the like; an stabilizing agent, such as an amino acid or the like; and distilled water for injection or physiological saline to the compound of the present invention, sterilizing and filtering the mixture, and then filling an ampoule with the mixture. Further, an injection which is to be dissolved when it is used can be obtained by adding mannitol, dextran, gelatin and the like, and lyophilizing the mixture under vacuum. Alternatively, a powder-filled injection can be made. Also, an emulsion for injection can be made by adding an emulsifier such as lecithin, a polysorbate, polyoxyethylene hardened castor oil, macrogol or the like to the compound of the present invention and then emulsifying the mixture in water.

Furthermore, examples of the injection include liposome preparations and lipid microspheres which enable the improvements of solubility and a migration rate to a target organ. In particular, nanosphere-liposome (lipid ultrafine particle) can not only increase a concentration in blood without being taken into reticuloendothelial tissues and lower a minimum effective dose required for exhibiting a pharmaceutical effect, but also pass a blood-brain barrier by about 10 times easier, so that it is suitable when it is used for treating cerebral neuronal diseases. The liposome preparation can be prepared according to a known liposome preparation method (C. G. Knight, *Liposomes: From Physical Structure to Therapeutic Applications*, pp. 51–82, Elsevier, Amsterdam (1981); *Proc. Natl. Acad. Sci., USA*, 75: 4194 (1978)).

That is, examples of an amphipathic substance forming a liposome membrane include phospholipids, such as natural phospholipids (e.g., yolk lecithin, soybean lecithin, sphingomyelin, phosphatidyl serine, phosphatidyl glycerol, phosphatidyl inositol, diphosphatidyl glycerol, phosphatidyl ethanolamine, cardiolipin, etc.), synthetic phospholipids (e.g., distearoyl phosphatidyl choline, dipalmitoyl phosphatidyl choline, dipalmitoyl phosphatidyl ethanolamine, etc.) or the like. Furthermore, in order to improve membrane stability, fluidity and membrane permeability of the medicament, known various additives can be added. Examples include cholesterols (e.g., cholesterol, ergosterol, phytosterol, sitosterol, stigmasterol, etc.), substances which are known to impart negative charge to liposome (e.g., phosphatidic acid, dicetyl phosphate, etc.), substances which are known to impart positive charge (e.g., stearylamine, stearylamine acetate, etc.), antioxidants (e.g., tocopherol, etc.), oily substances (e.g., soybean oil, cottonseed oil, sesame oil, liver oil, etc.) and the like.

Preparation of liposome can be carried out according to, for example, the following method. The above amphipathic substance, additives and the compound of the present invention are dissolved in an organic solvent (e.g., single solvent, such as chloroform, dichloromethane, ethanol, methanol, hexane or the like, or a mixed solvent thereof) respectively, both solutions are mixed, the organic solvent is removed in a vessel, such as a flask or the like, in the presence of an inert gas (e.g., nitrogen gas, argon gas, etc.), and a thin membrane is attached to the wall of the vessel. Then, this thin membrane is added to a suitable aqueous medium (e.g., physiological saline, a buffer, a phosphate buffered physiological saline, etc.), and the mixture was stirred by means of a stirrer. In order to obtain liposome having a small particle size, the mixture was further dispersed by use of an ultrasonic emulsifier, a pressurization type emulsifier, a French press cell pulverizer or the like. As described above, preparation of liposome proceeds by treating, with a membrane filter, a liquid in which the amphipathic substance and the like required for preparation of liposome and the compound of the present invention are dispersed in the aqueous medium to obtain nanosphere-liposome (lipid ultrafine particle; a particle size of about 25 to 50 nm) in which a particle size distribution is controlled. Furthermore, liposome can be subjected to fractionation treatment, such as ultrafiltration, centrifugation, gel filtration or the like, to remove the medicament which is not supported.

Furthermore, the liposome can be made to pass a blood-brain barrier easily by supporting an aminoalcohol derivative of formula (I), the compound of the present invention on liposome having, on a membrane thereof, a glucose residue, a tyrosine residue, a mannose residue or sulfatide obtained by adding β-octylglucoside, L-tyrosin-7-amido-4-methylcoumarin, phenylaminomannoside or sulfatide as a membrane-forming substance in addition to the above amphipathic substance and additives (as to a method itself, see JP-A-4-69332).

The lipid microsphere is obtained by dissolving the compound of the present invention in soybean oil, sesame oil or the like, stirring by means of a stirrer after the addition of a natural phospholipid, glycerin, water and the like, and further dispersing the mixture by use of an ultrasonic emulsifier, a pressurization type emulsifier, a French press cell pulverizer or the like.

The intrarectal preparation can be obtained by adding a base for a suppository such as mono-, di- or triglyceride of cacao fatty acid, polyethylene glycol or the like to the compound of the present invention, then melting the mixture by heating, pouring it into a mold and cooling it, or dissolving the compound of the present invention in polyethylene glycol, soybean oil or the like and then covering the mixture with a gelatin film.

The endermic preparation can be obtained by adding white petrolatum, beeswax, liquid paraffin, polyethylene glycol or the like to the compound of the present invention, heating the mixture, if necessary, and kneading it.

A tape preparation can be obtained by kneading the compound of the present invention with an adhesive, such as rosin, an alkyl acrylate polymer or the like, and spreading the mixture on non-woven fabric or the like.

The inhalation can be obtained by, for example, dissolving or dispersing the compound of the present invention in a propellant, such as a pharmaceutically acceptable inert gas or the like, and filling a pressure container with the mixture.

In the case that the compound of the present invention is used as an agent for treating neuronal diseases, particularly an agent for protecting brain or an agent for potentiating and protecting cranial nerves, an injection is preferable and an intravenous injection is more preferable. Such injections can be a lipid microsphere preparation or a preparation containing a surfactant in consideration of the distribution ability of the compound of the present invention to brain.

Method for Administration:

The method for administering a medicament containing the compound of the present invention as an active ingredient is not particularly limited, but when it is used for treating neuronal diseases caused by disorders of central nervous system, preferred is injection, such as intramuscular injection, intravenous injection, hypodermic injection, intraperitoneal injection or the like, intrarectal administration, intrapulmonary administration, ophthalmic administration, oral administration, or the like. Furthermore, when it is used for treating neuronal diseases caused by disorders of peripheral nervous system, preferred is intramuscular injection, endermic administration, ophthalmic administration, oral administration, or the like.

The dose can be suitably determined depending on age, health condition, body weight and the like of a patient, but the compound of the present invention is generally administered in an amount of 0.25 to 200 mg/kg, preferably 0.5 to 100 mg/kg by one dose or divided doses per day.

The aminoalcohol derivative represented by formula (I) or pharmaceutically acceptable salt thereof which is the compound of the present invention has a property participating the action of controlling glycolipid biosynthesis and thus has utility as a medicament based on the property, so that it is possible to provide an effective medicament containing the compound of the present invention. Among the compounds of the present invention, the compound having an effect of accelerating synapse formation and/or an action of accelerating glycolipid biosynthesis is especially expected to have an effect of accelerating nurite extension, an effect of preventing neurocyte death, and an effect of activating MAPkinase, and therefore promising as an agent for treating neuronal diseases. The compound is effective as an agent for treating diseases of central nervous system, particularly an agent for protecting brain or an agent for potentiating and protecting cranial nerves, for example, for the treatment of sequelae of cerebrovascular accident, and as an agent for treating diseases of peripheral nervous system, for example, for the treatment of polyneuropathy caused by cacochymia, mechanical neuropathy or toxic neuropathy.

The present invention will be explained in detail with reference to the examples, but the present invention is not limited thereto.

SYNTHETIC EXAMPLES

The synthetic examples of the compounds of the present invention are shown in Examples 1 to 28.

By the way, the synthetic examples of the intermediates of compounds of the present invention are shown as Production Examples. The reaction was carried out at room temperature unless otherwise indicated.

Furthermore, the products in Examples and Production Examples were identified based on nuclear magnetic resonance spectra.

The compounds synthesized in Examples of the present invention are all L-threo-isomers, and represented by the following formula (I)'. In the formula, * and R have the same meanings as described above.

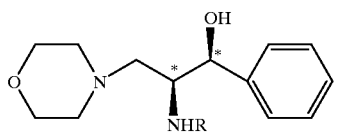

(I)'

The symbols in the following examples have the following meanings, respectively.

EDC: 1-Ethyl-3-(3-dimethylaminopropyl) carbodiimide hydrochloride
Z: Benzyloxycarbonyl group
L-PDMP: (1S,2S)-1-phenyl-2-decanoylamino-3-morpholino-1-propanol
$^{14}$C–Gal: D-[1–$^{14}$C]galactose
EDTA: Ethylenediamine tetraacetate
PBS: Dulbecco phosphate buffer salt solution
DMSO: Dimethylsulfoxide Example 1

Synthesis of (1S,2S) -2-benzyloxycarbonylglycylamino-3-morpholino-1-phenyl-1-propanol Methylene chloride (25 ml), Z-glycine (635.4 mg, 3.04 mmol), N-hydroxysuccinimide (699.3 mg, 6.08 mmol) and EDC (582.3 mg, 3.04 mmol) were added to (1S,2S)-2-amino-3-morpholino-1-phenyl-1-propanol (716.5 mg, 3.04 mmol), followed by stirring for 18 hours. Then, Z-glycine (635.3 mg, 3.04 mmol) and triethylamine (846 µl, 6.08 mmol) were added thereto, followed by further stirring for 16 hours. A saturated sodium hydrogen carbonate solution (70 ml) was added to the reaction solution, followed by extraction with ethyl acetate (100 ml). After washed with water (70 ml) and saturated brine (70 ml) successively, the organic layer was dried over sodium sulfate and filtered, and the solvent was evaporated under reduced pressure. The resulting crude product was purified by silica gel column chromatography (chloroform:methanol=20:1) to obtain the title compound (494.0 mg, yield 38.1%) as colorless oil.

$^1$H-NMR(CDCl$_3$) δ: 7.39–7.25 (10H, m, aromatic), 6.43 (1H, brs, NH), 5.34 (1H, brs, NH), 5.11 (2H, m, COOCH$_2$), 4.96 (1H, d, J=2.93 Hz, H-1), 4.29 (1H, m, H-2), 3.76 (2H, m, COCH$_2$—NH), 3.69 (4H, m, (CH$_2$)$_2$O), 2.55 (6H, m, CH$_2$N(CH$_2$)$_2$)
$^{13}$C-NMR(CDCl$_3$) δ: 169.2, 156.5, 140.6, 136.0, 129.1, 129.0, 128.6, 128.4, 128.3, 128.1, 127.8, 126.6, 126.0, 75.1, 67.3, 66.9, 59.7, 54.4, 51.2, 44.7

Example 2

Synthesis of (1S,2S)-2-benzyloxycarbonylglycylglycylamino-3-morpholino-1-phenyl-1-propanol A mixed solvent of methylene chloride:methanol=1:1 (5 ml) and triethylamine (274 µl, 1.97 mmol) were added to (1S,2S)-2-amino-3-morpholino-1-phenyl-1-propanol (232 mg, 0.98 mmol) to prepare Solution A2. Also, a mixed solvent of methylene chloride:methanol=1:1 (5 ml) and 1-hydroxybenzotriazole (263.9 mg, 0.99 mmol) were added to Z-glycylglycine (262.0 mg, 0.98 mmol) to prepare Solution B2. Solutions A2 and B2 were mixed and EDC (189.8 mg, 0.99 mmol) was added thereto, followed by stirring for 18 hours. Then, Z-glycylglycine (260.0 mg, 0.98 mmol) and 1-hydroxybenzotriazole (264.6 mg, 1.00 mmol) were added thereto, followed by further stirring for 3 hours. A saturated sodium hydrogen carbonate solution (70 ml) was added to the reaction solution, followed by extraction with ethyl acetate (100 ml). After washed with water (70 ml) and saturated brine (70 ml) successively, the organic layer was dried over sodium sulfate and filtered, and the solvent was evaporated under reduced pressure. The resulting crude product was purified by silica gel column chromatography (chloroform:methanol=20:1) to obtain the title compound (90.0 mg, yield 19.0%) as colorless oil.

$^1$H-NMR(CDCl$_3$) δ: 7.33–7.20 (10H, m, aromatic), 6.94 (1H, brs, NH), 6.05 (1H, brs, NH), 5.04 (2H, m, COOCH$_2$), 4.88 (1H, d, J=3.42 Hz, H-1), 4.28 (1H, m, H-2), 3.8 (4H, m, COCH$_2$—NH), 3.62 (4H, brs, (CH$_2$)$_2$O), 2.45 (6H, m, CH$_2$N(CH$_2$)$_2$)
$^{13}$C-NMR(CDCl$_3$) δ: 169.8, 169.0, 156.7, 141.0, 136.0, 128.5, 128.2, 127.9, 127.6, 126.1, 74.2, 67.1, 66.7, 59.4, 54.0, 51.5, 44.3, 42.9

Example 3

Synthesis of (1S,2S)-2-(n-butoxy) carbonylglycylamino-3-morpholino-1-phenyl-1-propanol Methanol (3 ml), triethylamine (178 µl, 1.28 mmol) and n-butyl chloroformate (100 µl, 0.77 mmol) were added to (1S,2S)-2-glycylamino-3-morpholino-1-phenyl-1-propanol (188.7 mg, 0.64 mmol) obtained in Production Example 1 described below, followed by stirring for 15 hours. A saturated sodium hydrogen carbonate solution (35 ml) was added to the reaction solution, followed by extraction with ethyl acetate (50 ml). After washed with water (35 ml) and saturated brine (35 ml) successively, the organic layer was dried over sodium sulfate and filtered, and the solvent was evaporated under reduced pressure. The resulting crude product was purified by silica gel column chromatography (ethyl acetate, ethyl acetate:methanol=20:1) to obtain the title compound (160.9 mg, yield 64.0%) as colorless oil.

$^1$H-NMR(CDCl$_3$) δ: 7.33–7.23 (5H, m, aromatic), 6.67 (1H, brs, NH), 5.61 (1H, brs, NH), 4.91 (1H, s, H-1), 4.26 (1H, m, H-2), 4.03 (2H, t, COOCH$_2$), 3.70–3.66 (6H, m, COCH$_2$—NH and (CH$_2$)$_2$O), 2.58–2.39 (6H, m, CH$_2$N (CH$_2$)$_2$), 1.58 (2H, m, COOCH$_2$CH$_2$), 1.36 (2H, m, CH$_2$—CH$_3$), 0.92 (3H, t, CH$_3$)
$^{13}$C-NMR(CDCl$_3$) δ: 169.5, 156.8, 140.8, 128.2, 127.5, 126.0, 74.3, 66.7, 65.2, 59.3, 54.0, 51.1, 44.3, 30.8, 18.8, 13.6

Production Example 1

Production of (1S,2S)-2-glycylamino-3-morpholino-1-phenyl-1-propanol (1S,2S)-2-Benzyloxycarbonylglycylamino-3-morpholino-1-phenyl-1-propanol (478.7 mg, 1.12 mmol) prepared in Example 1 was dissolved in methanol (10 ml), and 10% palladium/carbon (119.2 mg, 10.0 mol %) was added thereto, followed by stirring for 6 hours under a hydrogen atmosphere. The palladium/carbon was removed by filtration and the filtrate was concentrated to obtain the title compound.

Example 4

Synthesis of (1S,2S)-2-(n-hexanoyl)glycylamino-3-morpholino-1-phenyl-1-propanol

Methanol (3 ml), triethylamine (115 μl, 0.83 mmol) and n-hexanoyl chloride (114 μl, 0.83 mmol) were added to (1S,2S)-2-glycylamino-3-morpholino-1-phenyl-1-propanol (201.8 mg, 0.69 mmol) obtained in Production Example 1, followed by stirring for 3 hours. A saturated sodium hydrogen carbonate solution (35 ml) was added to the reaction solution, followed by extraction with ethyl acetate (50 ml). After washed with water (35 ml) and saturated brine (35 ml) successively, the organic layer was dried over sodium sulfate and filtered, and the solvent was evaporated under reduced pressure. The resulting crude product was purified by silica gel column chromatography (chloroform:methanol=20:1) to obtain the title compound (120.9 mg, yield 44.8%) as colorless oil.
$^1$H-NMR(CDCl$_3$) δ: 7.35–7.24 (5H, m, aromatic), 6.68 (1H, brs, NH), 6.39 (1H, brs, NH), 4.97 (1H, d, J=2.93 Hz, H-1), 4.31 (1H, m, H-2), 3.79 (2H, m, COCH$_2$—NH), 3.71 (4H, m, (CH$_2$)$_2$O), 2.66–2.47 (6H, m, CH$_2$N(CH$_2$)$_2$), 2.18 (2H, t, COCH$_2$CH$_2$), 1.59 (2H, m, COCH$_2$CH$_2$), 1.30 (4H, m, (CH$_2$)$_2$—CH$_3$), 0.89 (3H, t, CH$_3$)
$^{13}$C-NMR(CDCl$_3$) δ: 173.8, 169.1, 140.9, 128.3, 127.6, 126.0, 74.5, 66.9, 59.8, 54.3, 51.3, 43.2, 36.2, 31.4, 25.2, 22.3, 13.9

Example 5

Synthesis of (1S,2S)-2-(n-butoxy)butanedioylamino-3-morpholino-1-phenyl-1-propanol Methylene chloride (5 ml) and triethylamine (300 μl, 2.16 mmol) were added to (1S,2S)-2-amino-3-morpholino-1-phenyl-1-propanol (255.2 mg, 1.08 mmol) to prepare Solution A5. Also, methylene chloride (5 ml) and N-hydroxysuccinimide (263.9 mg, 2.16 mmol) were added to mono(n-butyl) ester of succinic acid (196.0 mg, 1.13 mmol) to prepare Solution B5. Solutions A5 and B5 were mixed and EDC (207.5 mg, 1.08 mmol) was added thereto, followed by stirring for 18 hours. A saturated sodium hydrogen carbonate solution (70 ml) was added to the reaction solution, followed by extraction with ethyl acetate (100 ml). After washed with water (70 ml) and saturated brine (70 ml) successively, the organic layer was dried over sodium sulfate and filtered, and the solvent was evaporated under reduced pressure. The resulting crude product was purified by silica gel column chromatography (chloroform:methanol=20:1) to obtain the title compound (70.7 mg, yield 16.7%) as colorless oil.
$^1$H-NMR(CDCl$_3$) δ: 7.37–7.26 (5H, m, aromatic), 6.06 (1H, d, J=7.32 Hz, NH), 4.95 (1H, d, J=3.90 Hz, H-1), 4.30 (1H, m, H-2), 4.05 (2H, t, COOCH$_2$), 3.73 (4H, m, (CH$_2$)$_2$O), 2.66–2.35 (10H, m, CH$_2$N(CH$_2$)$_2$ and COCH$_2$), 1.59 (2H, m, COOCH$_2$CH$_2$), 1.36 (2H, m, CH$_2$—CH$_3$), 0.93 (3H, t, CH$_3$)
$^{13}$C-NMR(CDCl$_3$) δ: 172.9, 171.9, 140.8, 128.4, 127.7, 126.1, 75.3, 66.9, 64.7, 59.7, 54.3, 51.1, 31.0, 30.6, 29.4, 19.1, 13.7

Example 6

Synthesis of (1S,2S)-2-ethoxyhexanedioylamino-3-morpholino-1-phenyl-1-propanol

Methylene chloride (40 ml), monoethyl ester of adipic acid (1.986 g, 11.40 mmol) and EDC (2.227 g, 11.62 mmol) were added to (1S,2S)-2-amino-3-morpholino-1-phenyl-1-propanol (2.858 g, 11.13 mmol), followed by stirring for 16 hours. After evaporating the solvent under reduced pressure, a saturated sodium hydrogen carbonate solution (90 ml) was added, followed by extraction with ethyl acetate (150 ml). After washed with water (90 ml) and saturated brine (90 ml) successively, the organic layer was dried over sodium sulfate and filtered, and the solvent was evaporated under reduced pressure. The resulting crude product was purified by silica gel column chromatography (chloroform:methanol=20:1) to obtain the title compound (3.855 g, yield 88.4%) as colorless oil.
$^1$H-NMR(CDCl$_3$) δ: 7.36–7.25 (5H, m, aromatic), 5.94 (1H, d, J=7.81 Hz, NH), 4.95 (1H, d, J=3.42 Hz, H-1), 4.29 (1H, m, H-2), 4.11 (2H, m, COO—CH$_2$), 3.71 (4H, m, (CH$_2$)$_2$O), 2.61–2.45 (6H, m, N(CH$_2$)$_3$), 2.25 (2H, t, O—CO—CH$_2$), 2.11 (2H, t, NHCO—CH$_2$), 1.53 (4H, m, COCH$_2$—CH$_2$), 1.25 (3H, t, CH$_3$)

Example 7

Synthesis of (1S,2S)-2-isopropoxyhexanedioylamino-3-morpholino-1-phenyl-1-propanol Monoisopropyl ester of adipic acid (530.0 mg, 2.0 mmol), methylene chloride (10 ml), triethylamine (700 μl, 5.0 mmol) and EDC (580 mg, 3.0 mmol) were added to (1S,2S)-2-amino-3-morpholino-1-phenyl-1-propanol (472.0 mg, 2.0 mmol), followed by stirring overnight. Methylene chloride (100 ml) was added to the reaction solution. After washed with a saturated sodium hydrogen carbonate solution (50 ml), water (50 ml) and saturated brine (50 ml) successively, the organic layer was dried over sodium sulfate and filtered, and the solvent was evaporated under reduced pressure. The resulting crude product was purified by silica gel column chromatography (chloroform:ethanol=20:1) to obtain the title compound (416.0 mg, yield 51.0%) as colorless oil.
$^1$H-NMR(CDCl$_3$) δ: 7.38–7.26 (5H, m, aromatic), 5.90 (1H, d, J=7.33 Hz, NH), 4.99 (1H, m, CO—O—CH), 4.97 (1H, d, J=3.42 Hz, H-1), 4.30 (1H, m, H-2), 3.72 (4H, m, (CH$_2$)$_2$O), 2.61 and 2.50 (2H, dd, H-3), 2.57 (4H, m, N(CH$_2$)$_2$), 2.22 (2H, m, O—CO—CH$_2$), 2.12 (2H, m, CO—CH$_2$), 1.54 (4H, m, CO—CH$_2$—CH$_2$), 1.22 (6H, d, J=6.35, CH$_3$)
$^{13}$C-NMR(CDCl$_3$) δ: 173.1, 172.9, 140.9, 128.4, 127.7, 126.0, 75.4, 67.6, 66.9, 59.8, 54.4, 51.2, 36.2, 34.2, 24.9, 24.3, 21.8

Example 8

Synthesis of (1S,2S)-2-(n-butoxyhexanedioyl) amino-3-morpholino-1-phenyl-1-propanol Mono(n-butyl) ester of adipic acid (405 mg, 2.0 mmol), methylene chloride (12 ml), triethylamine (420 µl, 3.0 mmol) and EDC (580 mg, 3.0 mmol) were added to (1S, 2S)-2-amino-3-morpholino-1-phenyl-1-propanol (472.0 mg, 2.0 mmol), followed by stirring overnight. Methylene chloride (100 ml) was added to the reaction solution. After washed with a saturated sodium hydrogen carbonate solution (50 ml), water (50 ml) and saturated brine (50 ml) successively, the organic layer was dried over sodium sulfate and filtered, and the solvent was evaporated under reduced pressure. The resulting crude product was purified by silica gel column chromatography (chloroform:ethanol=20:1) to obtain the title compound (308 mg, yield 37.0%) as colorless oil.

$^1$H-NMR(CDCl$_3$) δ: 7.38–7.26 (5H, m, aromatic), 5.90 (1H, d, J=7.33 Hz, NH), 4.97 (1H, d, J=3.90 Hz, H-1), 4.30 (1H, m, H-2), 4.06 (2H, m, COO—CH$_2$), 3.73 (4H, m, (CH$_2$)$_2$O), 2.61 and 2.50 (2H, dd, H-3), 2.57 (4H, m, N(CH$_2$)$_2$), 2.26 (2H, t, O—CO—CH$_2$), 2.13 (2H, t, NHCO—CH$_2$), 1.60 (2H, m, COO—CH$_2$—CH$_2$) 1.55 (4H, m, CO—CH$_2$—CH$_2$), 1.37 (2H, m CH$_2$—CH$_3$), 0.93 (3H, t, CH$_3$)

$^{13}$C-NMR(CDCl$_3$) δ: 173.5, 173.1, 140.9, 128.4, 127.7, 126.0, 75.4, 67.0, 64.3, 59.8, 54.4, 51.2, 36.2, 33.9, 30.7, 25.0, 24.3, 19.1, 13.2

Example 9

Synthesis of (1S,2S)-2-(3-butylcarbamoyl) propionylamino-3-morpholino-1-phenyl-1-propanol Methylene chloride (25 ml), 3-butylcarbamoylpropionic acid (600 mg, 3.4 mmol), triethylamine (1.7 ml, 12.0 mmol) and EDC (1.0 g, 5.1 mmol) were added to (1S,2S)-2-amino-3-morpholino-1-phenyl-1-propanol (802.4 mg, 3.4 mmol), followed by stirring overnight. Methylene chloride (100 ml) was added to the reaction solution. After washed with a saturated sodium hydrogen carbonate solution (50 ml), water (50 ml) and saturated brine (50 ml) successively, the organic layer was dried over sodium sulfate and filtered, and the solvent was evaporated under reduced pressure. The resulting crude product was purified by silica gel column chromatography (chloroform:methanol=20:1) to obtain the title compound (962 mg, yield 71.0%) as colorless oil.

$^1$H-NMR(CDCl$_3$) δ: 7.38–7.26 (5H, m, aromatic), 6.28 (1H, d, J=7.81 Hz, NH), 5.81 (1H, brs, NH), 4.95 (1H, d, J=3.42 Hz, H-1), 4.30 (1H, m, H-2), 3.73 (4H, m, (CH$_2$)$_2$O), 3.19 (2H, m, CONH—CH$_2$), 2.6–2.5 (2H, dd, H-3), 2.56 (4H, m, N(CH$_2$)$_2$), 2.6–2.4 (4H, m, CO—CH$_2$), 1.45 (2H, m, CH$_2$—CH$_2$—CH$_3$), 1.32 (2H, m CH$_2$—CH$_3$), 0.91 (3H, t, CH$_3$)

Example 10

Synthesis of (1S,2S)-2-(N-butyl-N-methylamino) butanedioylamino-3-morpholino-1-phenyl-1-propanol Mono(N-butyl-N-methyl)amide of succinic acid (370 mg, 2.0 mmol), methylene chloride (10 ml), triethylamine (0.7 ml, 5.0 mmol) and EDC (580.0 mg, 3.0 mmol) were added to (1S,2S)-2-amino-3-morpholino-1-phenyl-1-propanol (472.0 mg, 2.0 mmol), followed by stirring overnight. Methylene chloride (100 ml) was added to the reaction solution. After washed with a saturated sodium hydrogen carbonate solution (50 ml), water (50 ml) and saturated brine (50 ml) successively, the organic layer was dried over sodium sulfate and filtered, and the solvent was evaporated under reduced pressure. The resulting crude product was purified by silica gel column chromatography (chloroform:ethanol=20:1) to obtain the title compound (532.9 mg, yield 66.0%) as colorless oil.

$^1$H-NMR(CDCl$_3$) δ: 7.38–7.26 (5H, m, aromatic), 6.49 (1H, d, J=6.84 Hz, NH), 4.93 (1H, d, J=3.91 Hz, H-1), 4.30 (1H, m, H-2), 3.73 (4H, m, (CH$_2$)$_2$O), 3.4–3.2 (2H, m, CONH—CH$_2$), 2.94 and 2.89 (3H, s, N—CH$_3$), 2.6–2.5 (2H, dd, H-3), 2.56 (4H, m, N(CH$_2$)$_2$), 2.6–2.4 (4H, m, CO—CH$_2$), 1.6–1.4 (2H, m, CH$_2$—CH$_2$—CH$_3$) 1.4–1.2 (2H, m, CH$_2$—CH$_3$), 0.94 and 0.92 (3H, m CH$_2$—CH$_3$)

$^{13}$C-NMR(CDCl$_3$) δ: 173.1, 171.4, 141.0, 128.2, 127.5, 126.2, 75.6, 66.9, 59.6, 54.3, 51.1, 49.6, 47.7, 35.1, 33.5, 31.6, 31.5, 30.3, 29.4, 29.2, 28.5, 19.9, 13.8

Example 11

Synthesis of (1S,2S)-2-(5-ethylcarbamoyl) pentanoylamino-3-morpholino-1-phenyl-1-propanol Methylene chloride (160 ml), 5-ethylcarbamoylpentanoic acid (3.46 g, 20.0 mmol), triethylamine (6.4 ml, 46.0 mmol) and EDC (4.98 g, 26.0 mmol) were added to (1S,2S)-2-amino-3-morpholino-1-phenyl-1-propanol (4.72 g, 20.0 mmol), followed by stirring overnight. Methylene chloride (350 ml) was added to the reaction solution. After washed with a saturated sodium hydrogen carbonate solution (250 ml), water (250 ml) and saturated brine (250 ml) successively, the organic layer was dried over sodium sulfate and filtered, and the solvent was evaporated under reduced pressure. The resulting crude product was purified by silica gel column chromatography (chloroform:methanol=20:1) to obtain the title compound (1.02 g, yield 13.0%) as colorless oil.

$^1$H-NMR(CDCl$_3$) δ: 7.38–7.26 (5H, m, aromatic), 6.03 (1H, d, J=7.33 Hz, NH), 5.57 (1H, brs, NH), 4.97 (1H, d, J=3.90 Hz, H-1), 4.31 (1H, m, H-2), 3.73 (4H, m, (CH$_2$)$_2$O), 3.26 (2H, m, CH$_2$—CH$_3$), 2.61 and 2.50 (2H, dd, H-3), 2.56 (4H, m, N(CH$_2$)$_2$), 2.1 (4H, m, CO—CH$_2$), 1.54 (4H, m, CO—CH$_2$—CH$_2$), 1.13 (3H, t, CH$_3$)

Example 12

Synthesis of (1S,2S)-2-(5-cyclohexylcarbamoyl) pentanoylamino-3-morpholino-1-phenyl-1-propanol A mixed solvent of methylene chloride:methanol=4:1 (10 ml), 5-cyclohexylcarbamoylpentanoic acid (546.0 mg, 2.4 mmol), triethylamine (620 µl, 4.4 mmol) and EDC (460 mg, 2.4 mmol) were added to (1S,2S)-2-amino-3-morpholino-1-phenyl-1-propanol (472.0 mg, 2.0 mmol), followed by stirring overnight. Methylene chloride (100 ml) was added to the reaction solution. After washed with a saturated sodium hydrogen carbonate solution (50 ml), water (50 ml) and saturated brine (50 ml) successively, the organic layer was dried over sodium sulfate and filtered, and the solvent was evaporated under reduced pressure. The resulting crude product was purified by silica gel column chromatography (chloroform:methanol=10:1) to obtain the title compound (607 mg, yield 68.0%) as colorless oil.

$^1$H-NMR(CDCl$_3$) δ: 7.38–7.26 (5H, m, aromatic), 6.04 (1H, d, J=7.81 Hz, NH), 5.42 (1H, d, J=7.81 Hz, NH), 4.97 (1H, d, J=3.91 Hz, H-1), 4.32 (1H, m, H-2), 3.70 (4H, m, (CH$_2$)$_2$O), 2.61 and 2.50 (2H, dd, H-3), 2.58 (4H, m, N(CH$_2$)$_2$), 2.1 (4H, m, CO—CH$_2$), 1.6–1.5 (4H, m, CO—CH$_2$—CH$_2$), 1.4–1.3 (4H, m, CH—CH$_2$), 1.2–1.0 (6H, m, (CH$_2$)$_3$) $^{13}$C-NMR(CDCl$_3$) δ: 173.3, 171.6, 141.0, 128.4, 127.7, 126.1, 75.4, 67.0, 59.8, 54.4, 51.2, 48.2, 36.3, 36.1, 33.2, 25.5, 24.9, 24.8

Example 13

Synthesis of (1S,2S)-2-(5-hexylcarbamoyl)pentanoylamino-3-morpholino-1-phenyl-1-propanol Methylene chloride (20 ml), 5-hexylcarbamoylpentanoic acid (708.6 mg, 3.094 mmol) and EDC (621.7 mg, 3.243 mmol) were added to (1S,2S)-2-amino-3-morpholino-1-phenyl-1-propanol (703.1 mg, 2.979 mmol), followed by stirring for 18 hours. After evaporating the solvent under reduced pressure, a saturated sodium hydrogen carbonate solution (30 ml) was added, followed by extraction with ethyl acetate (50 ml). After washed with water (30 ml) and saturated brine (30 ml) successively, the organic layer was dried over sodium sulfate and filtered, and the solvent was evaporated under reduced pressure. The resulting crude product was purified by silica gel column chromatography (chloroform:methanol=20:1) to obtain the title compound (292.2 mg, yield 21.9%) as colorless oil.
$^1$H-NMR(CDCl$_3$) δ: 7.36–7.25 (5H, m, aromatic), 6.07 (1H, d, J=7.33 Hz, NH), 5.65 (1H, brs, NH), 4.96 (1H, d, J=3.41 Hz, H-1), 4.31 (1H, m, H-2), 3.72 (4H, m, (CH$_2$)$_2$O), 3.21 (2H, m, NH-CH$_2$), 2.62–2.47 (6H, m, CH$_2$N(CH$_2$)$_2$), 2.13–2.08 (4H, m, COCH$_2$), 1.55–1.44 (6H, m, COCH$_2$—CH$_2$, NH—CH$_2$CH$_2$), 1.29 (6H, m, CH$_2$(CH$_2$)$_3$CH$_2$), 0.89 (3H, t CH$_3$)
$^{13}$C-NMR(CDCl$_3$) δ: 173.2, 172.5, 141.0, 128.3, 127.6, 126.0, 75.2, 66.9, 59.7, 54.3, 51.2, 39.5, 36.0, 31.4, 29.5, 26.6, 24.8, 22.5, 14.0

Example 14

Synthesis of (1S,2S)-2-(9-butylcarbamoyl)nonanoylamino-3-morpholino-1-phenyl-1-propanol Methylene chloride (20 ml), 9-(n-butyl)carbamoylnonanoic acid (1063.1 mg, 4.136 mmol) and EDC (1546.1 mg, 8.065 mmol) were added to (1S,2S)-2-amino-3-morpholino-1-phenyl-1-propanol (920.8 mg, 3.901 mmol), followed by stirring for 21 hours. After evaporating the solvent under reduced pressure, a saturated sodium hydrogen carbonate solution (100 ml) was added, followed by extraction with ethyl acetate (100 ml). After washed with water (100 ml) and saturated brine (100 ml) successively, the organic layer was dried over sodium sulfate and filtered, and the solvent was evaporated under reduced pressure. The resulting crude product was purified by silica gel column chromatography (chloroform:methanol=20:1) to obtain the title compound (442.3 mg, yield 23.9%) as colorless oil.
$^1$H-NMR(CDCl$_3$) δ: 7.37–7.26 (5H, m, aromatic), 5.91 (1H, d, J=6.84 Hz, NH), 5.50 (1H, brs, NH), 4.96 (1H, d, J=3.42 Hz, H-1), 4.28 (1H, m, H-2), 3.72 (4H, m, (CH$_2$)$_2$O), 3.23 (2H, m, NH—CH$_2$), 2.62–2.46 (6H, m, CH$_2$N(CH$_2$)$_2$), 2.11 (4H, m, COCH$_2$), 1.60 (2H, m, COCH$_2$—CH$_2$), 1.47 (4H, m, COCH$_2$—CH$_2$, NH—CH$_2$CH$_2$), 1.34 and 1.26 (10 H, m, CH$_2$(CH$_2$)$_4$CH$_2$, CH$_2$—CH$_3$), 0.92 (3H, t CH$_3$)
$^{13}$C-NMR(CDCl$_3$) δ: 173.7, 173.0, 141.0, 128.4, 127.6, 126.0, 75.5, 66.9, 59.8, 54.3, 51.2, 39.2, 36.8, 36.7, 31.7, 29.1, 29.0, 25.7, 25.6, 25.5, 20.1, 13.7

Example 15

Synthesis of (1S,2S)-2-(9-hexylcarbamoyl)nonanoylamino-3-morpholino-1-phenyl-1-propanol Methylene chloride (25 ml), 9-(n-hexyl)carbamoylnonanoic acid (908.2 mg, 3.187 mmol), ethanol (3 ml) and EDC (628.5 mg, 3.278 mmol) were added to (1S,2S)-2-amino-3-morpholino-1-phenyl-1-propanol (732.1 mg, 3.102 mmol), followed by stirring for 17 hours. Then, EDC (765.8 mg, 3.995 mmol) and triethylamine (0.90 ml, 6.469 mmol) were further added, followed by stirring for 14 hours. After evaporating the solvent under reduced pressure, a saturated sodium hydrogen carbonate solution (100 ml) was added, followed by extraction with ethyl acetate (100 ml). After washed with water (100 ml) and saturated brine (100 ml) successively, the organic layer was dried over sodium sulfate and filtered, and the solvent was evaporated under reduced pressure. The resulting crude product was purified by silica gel column chromatography (chloroform:methanol=20:1) to obtain the title compound (468.1 mg, yield 30.0%) as colorless oil.
$^1$H-NMR(CDCl$_3$) δ: 7.37–7.26 (5H, m, aromatic), 5.91 (1H, d, J=7.32 Hz, NH), 5.49 (1H, brs, NH), 4.96 (1H, d, J=3.91 Hz, H-1), 4.29 (1H, m, H-2), 3.73 (4H, m, (CH$_2$)$_2$O), 3.22 (2H, m, NH—CH$_2$), 2.62–2.47 (6H, m, CH$_2$N(CH$_2$)$_2$), 2.15–2.08 (4H, m, COCH$_2$), 1.60 (2H, m, NHCH$_2$—CH$_2$), 1.48 (4H, m, COCH$_2$—CH$_2$), 1.29–1.24 (14H, m, CH$_2$(CH$_2$)$_4$CH$_2$, (CH$_2$)$_3$—CH$_3$), 0.88 (3H, t, CH$_3$)
$^{13}$C-NMR(CDCl$_3$) δ: 173.7, 173.0, 140.9, 128.4, 127.6, 126.0, 75.4, 66.9, 59.8, 54.3, 51.2, 39.5, 36.8, 36.7, 31.5, 29.6, 29.1, 29.0, 28.9, 26.6, 25.7, 25.5, 22.5, 14.0

Example 16

Synthesis of (1S,2S)-2-(N,N-diethanolamino)decanedioylamino-3-morpholino-1-phenyl-1-propanol Methylene chloride (5 ml), ethanol (5 ml) and N-hydroxysuccinimde (394.8 mg, 3.433 nmol) were added to mono(diethanol)amide of sebacic acid (969.2 mg, 3.354 mmol) to prepare Solution A16. Also, ethanol (10 ml) was added to (1S,2S)-2-amino-3-morpholino-1-phenyl-1-propanol (735.1 mg, 3.115 mmol) to prepare Solution B16. Solutions A16 and B16 were mixed and EDC (760.8 mg, 3.969 mmol) was added thereto, followed by stirring for 90 minutes. Then, EDC (362.8 mg, 1.893 mmol) was added thereto, followed by further stirring for 17 hours. After evaporating the solvent under reduced pressure, a saturated sodium hydrogen carbonate solution (20 ml) was added, followed by extraction with ethyl acetate (50 ml). After washed with water (20 ml) and saturated brine (20 ml) successively, the organic layer was dried over sodium sulfate and filtered, and the solvent was evaporated under reduced pressure. The resulting crude product was purified by silica gel column chromatography (chloroform:ethyl acetate:methanol=9:10:1 and chloroform:methanol=20:1) to obtain the title compound (193.9 mg, yield 12.3%) as colorless oil.
$^1$H-NMR(CDCl$_3$) δ: 7.36–7.25 (5H, m, aromatic), 5.27 (1H, brs, NH), 5.06 (1H, d, J=5.86 Hz, NH), 4.82 (1H, d, J=4.88 Hz, H-1), 4.16–4.07 (1H, m, H-2), 3.83 (1H, t, CH$_2$—OH), 3.77 (1H, t, CH2—OH), 3.70 (4H, m, (CH$_2$)$_2$O), 3.55–3.35 (6H, m, CH$_2$—OH, CH$_2$CH$_2$—OH), 2.57–2.26 (10H, m, CH$_2$N(CH$_2$)$_2$ and COCH$_2$), 1.61 (4H, m, COCH$_2$CH$_2$), 1.30–1.23 (8H, m, CH$_2$(CH$_2$)$_4$CH$_2$)
13C-NMR (CDCl$_3$) δ: 175.6, 172.9, 141.2, 128.3, 127.6, 126.4, 76.5, 66.8, 61.7, 60.8, 60.7, 60.2, 59.8, 54.0, 52.1, 52.0, 50.5, 35.9, 34.6, 29.0, 25.1, 24.8

Example 17

Synthesis of (1S,2S)-2-(cyclohexane-4-hexylcarbamoyl-1-carbonyl)amino-3-morpholino-1-phenyl-1-propanol Cyclohexanedicarboxylic acid (1.72 g, 10.0 mmol), triethylamine (1.60 ml, 11.0 mmol) and EDC (420 mg, 2.2 mmol) were added to (1S,2S)-2-amino-3-morpholino-1-phenyl-1-propanol (472.0 mg, 2.0 mmol), followed by stirring overnight. After evaporating the solvent under reduced pressure, a saturated sodium hydrogen carbonate solution (50 ml) was added, and the mixture was concentrated. A mixed solvent of chloroform:methanol=5:1 (60 ml) was added thereto and insoluble matter was removed by filtration. Thereafter, the filtrate was concentrated and the concentrate was purified by silica gel column chromatography (chloroform:methanol=9:1 and 5:1) to obtain an intermediary product (152 mg). Then, hexylamine (350 mg, 3.5 mmol), triethylamine (0.24 ml, 1.7 mmol) and EDC (330 mg, 1.7 mmol) were added to the intermediary product (135 mg, 0.35 mmol), followed by stirring overnight. Methylene chloride (100 ml) was added to the reaction solution. After washed with a saturated sodium hydrogen carbonate solution (50 ml), water (50 ml) and saturated brine (50 ml) successively, the organic layer was dried over sodium sulfate and filtered, and the solvent was evaporated under reduced pressure. The resulting crude product was purified by silica gel column chromatography (chloroform:methanol=9:1) to obtain the title compound (32.6 mg, yield 19.7%) as colorless oil.

$^1$H-NMR(CDCl$_3$) δ: 7.38–7.26 (5H, m, aromatic), 5.97 (1H, d, J=7.32 Hz, NH), 5.53 (1H, t, NH), 4.96 (1H, d, J=3.42 Hz, H-1), 4.28 (1H, m, H-2), 3.72 (4H, m, (CH$_2$)$_2$O), 3.2 (2H, q, CONH—CH$_2$), 2.60 and 2.49 (2H, dd, H-3), 2.56 (4H, m, N(CH2)$_2$), 2.0 (2H, m, CO—CH), 1.9–1.7 (8H, m, CH—CH$_2$), 1.6–1.2 (8H, m, CONH—CH$_2$(CH$_2$)$_4$), 0.88 (3H, t, (CH$_2$)$_3$)

$^{13}$C-NMR(CDCl$_3$) δ: 176.0, 175.3, 141.0, 128.4, 127.7, 126.1, 75.3, 67.0, 59.8, 54.4, 51.1, 44.7, 44.6, 39.4, 31.5, 29.6, 28.7, 28.6, 26.6, 22.6, 14.0

Example 18

Synthesis of (1S,2S)-2-(3-oxaheptanoyl)amino-3-morpholino-1-phenyl-1-propanol

Methylene chloride (20 ml), 3-oxaheptanoic acid (529.0 mg, 4.0 mmol), triethylamine (1.40 ml, 10.0 mmol) and EDC (1.15 g, 6.0 mmol) were added to (1S,2S)-2-amino-3-morpholino-1-phenyl-1-propanol (944.0 mg, 4.0 mmol), followed by stirring overnight. Methylene chloride (100 ml) was added to the reaction solution. After washed with a saturated sodium hydrogen carbonate solution (50 ml), water (50 ml) and saturated brine (50 ml) successively, the organic layer was dried over sodium sulfate and filtered, and the solvent was evaporated under reduced pressure. The resulting crude product was purified by silica gel column chromatography (chloroform:ethanol=30:1) to obtain the title compound (825 mg, yield 59%) as colorless oil.

$^1$H-NMR(CDCl$_3$) δ: 7.38–7.26 (5H, m, aromatic), 6.95 (1H, d, J=7.81 Hz, NH), 4.99 (1H, d, J=3.91 Hz, H-1), 4.35 (1H, m, H-2), 3.88 and 3.82 (2H, d, CO—CH$_2$), 3.74 (4H, m, (CH$_2$)$_2$O), 3.40 (2H, t, O—CH$_2$—(CH$_2$)$_2$—CH$_3$), 2.63 and 2.50 (2H, dd, H-3), 2.59 (4H, m, N(CH$_2$)$_2$), 1.55 (2H, m, CH$_2$—CH$_2$CH$_3$), 1.35 (2H, m, CH$_2$—CH$_3$), 0.93 (3H, t, CH$_3$)

$^{13}$C-NMR(CDCl$_3$) δ: 170.3, 140.7, 128.4, 127.7, 126.2, 75.6, 71.5, 70.1, 67.0, 59.8, 54.4, 50.3, 31.6, 19.2, 13.9

Example 19

Synthesis of (1S,2S)-2-(3,6-dioxadecanoyl)amino-3-morpholino-1-phenyl-1-propanol Methylene chloride (20 ml), 3,6-dioxadecanoic acid (705.0 mg, 4.0 mmol), triethylamine (1.40 ml, 10.0 mmol) and EDC (1.15 g, 6.0 mmol) were added to (1S,2S)-2-amino-3-morpholino-1-phenyl-1-propanol (944.0 mg, 4.0 mmol), followed by stirring overnight. Methylene chloride (100 ml) was added to the reaction solution. After washed with a saturated sodium hydrogen carbonate solution (50 ml), water (50 ml) and saturated brine (50 ml) successively, the organic layer was dried over sodium sulfate and filtered, and the solvent was evaporated under reduced pressure. The resulting crude product was purified by silica gel column chromatography (chloroform:ethanol=30:1) to obtain the title compound (815 mg, yield 52%) as colorless oil.

$^1$H-NMR(CDCl$_3$) δ: 7.38–7.26 (5H, m, aromatic), 7.06 (1H, d, J=7.82 Hz, NH), 4.99 (1H, d, J=3.91 Hz, H-1), 4.38 (1H, m, H-2), 3.96 and 3.89 (2H, d, CO—CH$_2$), 3.73 (4H, m, (CH$_2$)$_2$O), 3.52 (4H, m, O—CH$_2$—CH$_2$—O), 3.42 (2H, t, O—CH$_2$—(CH$_2$)$_2$—CH$_3$), 2.63 and 2.50 (2H, dd, H-3), 2.58 (4H, m, N(CH$_2$)$_2$), 1.54 (2H, m, CH$_2$—(CH$_2$)$_2$—CH$_3$), 1.34 (2H, m, CH$_2$—CH$_3$), 0.92 (3H, t, CH$_3$)

$^{13}$C-NMR(CDCl$_3$) δ: 170.2, 140.9, 128.3, 127.6, 126.2, 75.2, 71.3, 70.9, 70.3, 69.7, 66.9, 59.6, 54.3, 50.4, 31.6, 19.2, 13.9

Example 20

Synthesis of (1S,2S)-2-[4-(4-methoxyphenyl)butyryl]amino-3-morpholino-1-phenyl-1-propanol Methylene chloride (10 ml), 4-(4-methoxyphenyl)butanoic acid (388.0 mg, 2.0 mmol), triethylamine (0.70 ml, 5.0 mmol) and EDC (580 mg, 3.0 mmol) were added to (1S,2S)-2-amino-3-morpholino-1-phenyl-1-propanol (472.0 mg, 2.0 mmol), followed by stirring overnight. Methylene chloride (100 ml) was added to the reaction solution. After washed with a saturated sodium hydrogen carbonate solution (50 ml), water (50 ml) and saturated brine (50 ml) successively, the organic layer was dried over sodium sulfate and filtered, and the solvent was evaporated under reduced pressure. The resulting crude product was purified by silica gel column chromatography (chloroform:ethanol=20:1) to obtain the title compound (549 mg, yield 66%) as colorless oil.

$^1$H-NMR(CDCl$_3$) δ: 7.38–7.26 (5H, m, aromatic), 7.02 (2H, d, J=8.79 Hz, aromatic), 6.81 (2H, m, aromatic), 5.80 (1H, d, J=7.32 Hz, NH), 4.97 (1H, d, J=3.41 Hz, H-1), 4.31 (1H, m, H-2), 3.79 (3H, s, O—CH$_3$), 3.72 (4H, m, (CH$_2$)$_2$O), 2.61 and 2.49 (2H, dd, H-3), 2.56 (4H, m, N(CH$_2$)$_2$), 2.48 (2H, m, CO—CH$_2$), 2.10 (2H, m, CO(CH$_2$)$_2$CH$_2$), 1.82 (2H, m, COCH$_2$—CH$_2$)

$^{13}$C-NMR(CDCl$_3$) δ: 173.3, 157.9, 140.8, 133.3, 129.3, 128.4, 127.7, 126.0, 113.8, 75.4, 66.9, 59.9, 55.3, 54.4, 51.2, 35.7, 34.0, 27.2

Example 21

Synthesis of (1S,2S)-2-(3,6-dioxadodecanoyl)amino-3-morpholino-1-phenyl-1-propanol Methylene chloride (40 ml), 3,6-dioxadodecanoic acid (1.086 g, 5.325 mmol) and EDC (1.167 g, 6.090 mmol) were added to (1S,2S)-2-amino-3-morpholino-1-phenyl-1-propanol (959.1 mg, 4.064 mmol), followed by stirring for 3 hours. EDC (719.3 mg, 3.752 mmol) was added thereto and the mixture was further stirred for 3 days. After evaporating the solvent under reduced pressure, a saturated sodium hydrogen carbonate solution (70 ml) was added, followed by extraction with ethyl acetate (100 ml). After washed with water (70 ml) and saturated brine (70 ml) successively, the organic layer was dried over sodium sulfate and filtered, and the solvent was evaporated under reduced pressure. The resulting crude product was purified by silica gel column chromatography (chloroform:methanol=30:1) to obtain the title compound (812.3 mg, yield 47.4%) as colorless oil.
$^1$H-NMR(CDCl$_3$) δ: 7.37–7.25 (5H, m, aromatic), 7.05 (1H, d, J=8.31 Hz, NH), 4.98 (1H, d, J=3.91 Hz, H-1), 4.38 (1H, m, H-2), 3.92 (2H, m, CO—CH$_2$—O), 3.73 (4H, m, (CH$_2$)$_2$O), 3.52 (4H, m, O(CH$_2$)$_2$O), 3.41 (2H, t, OCH$_2$(CH$_2$)$_4$), 2.66–2.47 (6H, m, CH$_2$N(CH$_2$)$_2$), 1.53 (2H, m, CH$_2$(CH$_2$)$_3$CH$_3$), 1.29 (6H, m, CH$_2$(CH$_2$)$_3$CH$_3$), 0.89 (3H, t, CH$_3$)
$^{13}$C-NMR(CDCl$_3$) δ: 170.2, 140.9, 128.3, 127.5, 126.2, 75.2, 71.6, 71.0, 70.4, 69.6, 66.9, 59.6, 54.3, 50.4, 31.6, 29.5, 25.7, 22.6, 14.1

Example 22

Synthesis of (1S,2S)-2-(7-oxooctanoyl)amino-3-morpholino-1-phenyl-1-propanol

A mixed solvent of methylene chloride:methanol=9:1 (20 ml), 7-oxooctanoic acid (700 mg, 4.4 mmol), triethylamine (1.40 ml, 10.0 mmol) and EDC (1.15 g, 6.0 mmol) were added to (1S,2S)-2-amino-3-morpholino-1-phenyl-1-propanol (944.0 mg, 4.0 mmol), followed by stirring overnight. Methylene chloride (100 ml) was added to the reaction solution. After washed with a saturated sodium hydrogen carbonate solution (50 ml), water (50 ml) and saturated brine (50 ml) successively, the organic layer was dried over sodium sulfate and filtered, and the solvent was evaporated under reduced pressure. The resulting crude product was purified by silica gel column chromatography (chloroform:ethanol=20:1) to obtain the title compound (890 mg, yield 59%) as colorless oil.
$^1$H-NMR(CDCl$_3$) δ: 7.38–7.26 (5H, m, aromatic), 5.88 (1H, d, J=7.33 Hz, NH), 4.96 (1H, d, J=3.42 Hz, H-1), 4.28 (1H, m, H-2), 3.72 (4H, m, (CH$_2$)$_2$O), 2.61 and 2.49 (2H, dd, H-3), 2.56 (4H, m, N(CH$_2$)$_2$), 2.38 (2H, t, CO—CH$_2$), 2.12 (3H, S, CO—CH$_3$), 2.10 (2H, dt, CH$_3$COCH$_2$), 1.52 (4H, m, COCH$_2$CH$_2$), 1.18 (2H, m, CO (CH$_2$)$_2$CH$_2$)
$^{13}$C-NMR (CDCl$_3$) δ: 209.4, 173.4, 141.0, 128.4, 127.6, 126.0, 75.3, 67.0, 59.8, 54.4, 51.2, 43.3, 36.4, 29.9, 28.4, 25.4, 23.2

Example 23

Synthesis of (1S,2S)-2-(10-hydroxydecanoyl)amino-3-morpholino-1-phenyl-1-propanol Methylene chloride (20 ml), 10-hydroxydecanoic acid (377 mg, 2.0 mmol), triethylamine (0.70 ml, 5.0 mmol) and EDC (580 mg, 3.0 mmol) were added to (1S,2S)-2-amino-3-morpholino-1-phenyl-1-propanol (472.0 mg, 2.0 mmol), followed by stirring overnight. Methylene chloride (100 ml) was added to the reaction solution. After washed with a saturated sodium hydrogen carbonate solution (50 ml), water (50 ml) and saturated brine (50 ml) successively, the organic layer was dried over sodium sulfate and filtered, and the solvent was evaporated under reduced pressure. The resulting crude product was purified by silica gel column chromatography (chloroform:ethanol=20:1) to obtain the title compound (508 mg, yield 62%) as colorless oil.
$^1$H-NMR(CDCl$_3$) δ: 7.38–7.26 (5H, m, aromatic), 5.88 (1H, d, J=7.32 Hz, NH), 4.96 (1H, d, J=3.42 Hz, H-1), 4.29 (1H, m, H-2), 3.73 (4H, m, (CH$_2$)$_2$O), 3.62 (2H, m, CH$_2$—OH), 2.60 and 2.49 (2H, dd, H-3), 2.56 (4H, m, N(CH$_2$)$_2$), 2.10 (2H, m, CO—CH$_2$), 1.6–1.4 (4H, m, CH$_2$—CH$_2$—OH, CO—CH$_2$—CH$_2$), 1.4–1.2 (10H, m, (CH$_2$)$_5$)
$^{13}$C-NMR(CDCl$_3$) δ: 173.7, 140.9, 128.4, 127.7, 126.0, 75.5, 66.9, 63.0, 59.8, 54.4, 51.2, 36.4, 32.7, 29.3, 29.1, 29.0, 25.6

Example 24

Synthesis of (1S,2S)-2-methoxydecanedioylamino-3-morpholino-1-phenyl-1-propanol

Methylene chloride (40 ml), monomethyl ester of sebacic acid (1.13 g, 5.23 mmol) and EDC (1.51 g, 7.88 mmol) were added to (1S,2S)-2-amino-3-morpholino-1-phenyl-1-propanol (1.244 g, 5.27 mmol), followed by stirring for 15 hours. Then, EDC (1.10 g, 5.73 mmol) and triethylamine (1.0 ml, 7.19 mmol) were further added, followed by stirring for 22 hours. After evaporating the solvent under reduced pressure, a saturated sodium hydrogen carbonate solution (70 ml) was added, followed by extraction with ethyl acetate (100 ml). After washed with water (70 ml) and saturated brine (70 ml) successively, the organic layer was dried over sodium sulfate and filtered, and the solvent was evaporated under reduced pressure. The resulting crude product was purified by silica gel column chromatography (chloroform:ethyl acetate:methanol=9:10:1) to obtain the title compound (1.89 g, yield 82.7%) as colorless oil.
$^1$H-NMR(CDCl$_3$) δ: 7.37–7.25 (5H, m, aromatic), 5.85 (1H, d, J=7.32 Hz, NH), 4.96 (1H, d, J=3.42 Hz, H-1), 4.28 (1H, m, H-2), 3.72 (4H, m, (CH$_2$)$_2$O), 3.67 (3H, s, OCH$_3$), 2.63–2.47 (6H, m, CH$_2$N(CH$_2$)$_2$), 2.30 (2H, m, COCH$_2$), 2.09 (2H, m, COCH$_2$), 1.60 (2H, m, COCH$_2$—CH$_2$), 1.50 (2H, m, COCH$_2$—CH$_2$), 1.26 (8H, m, CH$_2$(CH$_2$)$_4$CH$_2$)

Example 25

Synthesis of (1S,2S)-2-(9-carboxynonanoyl)amino-3-morpholino-1-phenyl-1-propanol Methylene chloride (10 ml), triethylamine (190 μl, 1.37 mmol) and sebacic anhydride (292.4 mg, 1.59 mmol) were added to (1S,2S)-2-amino-3-morpholino-1-phenyl-1-propanol (316.2 mg, 1.34 mmol), followed by stirring for 5 hours. Then, the solvent was evaporated under reduced pressure. The resulting crude product was purified by silica gel column chromatography (chloroform:methanol=20:1 and chloroform:methanol=9:1) to obtain the title compound (171.1 mg, yield 30.4%) as colorless oil.
$^1$H-NMR(CDCl$_3$) δ: 7.36–7.25 (5H, m, aromatic), 6.50 (1H, d, J=7.82 Hz, NH), 4.94 (1H, d, J=3.91 Hz, H-1), 4.37 (1H, m, H-2), 3.80–3.69 (4H, m, (CH$_2$)$_2$O), 2.77–2.63 (6H, m, CH$_2$N(CH$_2$)$_2$), 2.30 (2H, m, COCH$_2$), 2.09 (2H, m, COCH$_2$), 1.61 (2H, m, COCH$_2$—CH$_2$), 1.48 (2H, m, COCH$_2$—CH$_2$), 1.30–1.16 (8H, m, CH$_2$(CH$_2$)$_4$CH$_2$)
$^{13}$C-NMR(CDCl$_3$) δ: 178.3, 174.1, 140.7, 128.4, 127.7, 126.0, 75.1, 66.2, 59.3, 53.9, 51.0, 36.5, 34.4, 28.9, 28.8, 25.4, 24.9, 24.8

Example 26

Synthesis of (1S,2S,12S)-2-(12-amino-7-aza-6-oxo-12-carboxydodecanoyl)amino-3-morpholino-1-phenyl-1-propanol The ester bond of (1S,2S)-2-ethoxyhexanedioylamino-3-morpholino-1-phenyl-1-propanol obtained in Example 6 was hydrolyzed to produce (1S,2S)-2-(5-carboxypentanoyl)amino-3-morpholino-1-phenyl-1-propanol (Intermediate product (26-1)). Then, the carboxyl group of the compound and the amino group of Nα-benzyloxycarbonyl-L-lysine methyl ester were condensed in a usual manner. The title compound was obtained by removing the protecting group finally.

Concretely, methanol (6 ml) and a 2 N sodium hydroxide solution (588 μl, 1.176 mmol) were added to (1S,2S)-2- ethoxyhexanedioylamino-3-morpholino-1-phenyl-1-propanol (230.6 mg, 0.588 mmol), followed by stirring at 40° C. one day and night.

Then, after neutralized with 2N hydrochloric acid, the solvent was evaporated under reduced pressure and the residue was desalted by gel filtration chromatography. Nα-Benzyloxycarbonyl-L-lysine methyl ester (202.9 mg, 0.690 mmol), methylene chloride (9 ml), ethanol (2 ml) and EDC (389.0 mg, 2.029 mmol) were added to the resulting Intermediate product (26-1) (212.4 mg, 0.583 mmol), followed by stirring for one day and night. Then, the solvent was evaporated under reduced pressure and ethyl acetate (70 ml) was added to the residue. After washed with a saturated sodium hydrogen carbonate solution (30 ml), water (30 ml) and saturated brine (30 ml) successively, the organic layer was dried over sodium sulfate and filtered, and the solvent was evaporated under reduced pressure. The resulting crude product was purified by silica gel column chromatography (chloroform:methanol=20:1) to obtain Intermediate product (26-2). Then, methanol (3 ml) and a 2N sodium hydroxide solution (320 μl, 0.64 mmol) were added to Intermediate product (26-2) (198.6 mg, 0.310 mmol), followed by stirring at 40° C. for 3 hours. Thereafter, 2 N hydrochloric acid (320 μl, 0.64 mmol) was added thereto, followed by stirring overnight. Then, 2 N hydrochloric acid (320 μl, 0.64 mmol) and 10% palladium/carbon (47.3 mg) were added thereto, followed by further stirring under a hydrogen atmosphere for one day and night. Finally, the solvent was evaporated under reduced pressure and the resulting crude product was purified by gel filtration chromatography (Sephadex LH-20 (Amersham Pharmacia Biotech), chloroform:methanol=2:1) to obtain the title compound (160.6 mg) as a colorless amorphous substance.

NMR (Intermediate Product 26-2)
$^1$H-NMR(CDCl$_3$) δ: 7.38–7.24 (10H, m, aromatic), 6.01 (1H, d, J=7.82 Hz, NH), 5.78 (1H, brs, NH), 5.54 (1H, d, J=8.30 Hz, NH), 5.09 (2H, s, COOCH$_2$), 4.96 (1H, d, J=3.91 Hz, H-1), 4.38–4.32 (2H, m, H-2 and NH$_2$—CH—CO), 3.74–3.70 (7H, m, (CH$_2$)$_2$O, OCH$_3$), 3.22 (2H, m, CONHCH$_2$), 2.61–2.45 (6H, m, CH$_2$N(CH$_2$)$_2$), 2.10 (4H, m, COCH$_2$), 1.83 (1H, m, CH$_2$), 1.69 (1H, m, CH$_2$), 1.52 (8H, m, CH$_2$), 1.37 (2H, m, CH$_2$)

NMR (Target Compound in Example 26)
$^1$H-NMR(CD$_3$OD) δ: 7.42 (2H, d, J=7.32 Hz, aromatic), 7.33 (2H, m, aromatic), 7.25 (1H, m, aromatic), 4.93 (1H, d, J=2.93 Hz, H-1), 4.62 (1H, m, NH$_2$—CH—CO), 4.06–3.92 (4H, m), 3.82–3.76 (2H, m), 3.54–3.46 (3H, m), 3.35–3.16 (4H, m), 2.23–2.14 (4H, m, COCH$_2$), 2.02–1.86 (2H, m, NH$_2$CHCH$_2$), 1.61–1.30 (8H, m, CH$_2$)
$^{13}$C-NMR(CD$_3$OD) δ: 176.8, 176.0, 171.8, 142.5, 129.3, 128.8, 127.3, 73.9, 64.8, 60.9, 58.3, 54.8, 53.9, 53.8, 52.9, 51.2, 51.1, 39.9, 36.5, 36.4, 31.1, 29.9, 26.2, 25.8, 23.4

Example 27

Synthesis of (1S,2S,16S)-2-(16-amino-11-aza-10-oxo-16-carboxyhexadecanoyl)amino-3-morpholino-1-phenyl-1-propanol Methanol (14 ml) and a 2 N sodium hydroxide solution (1335 μl, 2.670 mmol) were added to (1S,2S)-2-methoxydecanedioylamino-3-morpholino-1-phenyl-1-propanol (579.6 mg, 1.335 mmol) obtained in Example 24, followed by stirring at 40° C. for 16 hours. Then, after 2 N hydrochloric acid (1335 μl, 2.670 mmol) was added thereto, followed by stirring for 10 minutes, the solvent was concentrated under reduced pressure and the residue was subjected to desalination by gel filtration chromatography. Nα-Benzyloxycarbonyl-L-lysine methyl ester (394.2 mg, 1.341 mmol), methylene chloride (12 ml) and EDC (491.0 mg, 2.562 mmol) were added to the resulting Intermediate product (27-1) (475.2 mg, 1.131 mmol), followed by stirring for 14 hours. Then, the solvent was evaporated under reduced pressure and ethyl acetate (80 ml) was added to the residue. After washed with a saturated sodium hydrogen carbonate solution (50 ml), water (50 ml) and saturated brine (50 ml) successively, the organic layer was dried over sodium sulfate and filtered, and the solvent was evaporated under reduced pressure. The resulting crude product was purified by silica gel column chromatography (chloroform:methanol=20:1) to obtain an intermediary product (27-2). Then, methanol (6 ml) and a 2 N sodium hydroxide solution (640 μl, 1.28 mmol) were added to Intermediate product (27-2) (441.7 mg, 0.635 mmol), followed by stirring at 40° C. for 3 hours. Thereafter, 2 N hydrochloric acid (640 μl, 1.28 mmol) was added thereto, followed by stirring for one day and night. Then, 2 N hydrochloric acid (640 μl, 1.28 mmol) and 10% palladium/carbon (64.9 mg) were added thereto, followed by further stirring under a hydrogen atmosphere for one day and night. Finally, the solvent was evaporated under reduced pressure and the resulting crude product was purified by gel filtration chromatography (Sephadex LH-20 (manufactured by Amersham Pharmacia Biotech), chloroform:methanol=2:1) to obtain the title compound (366.7 mg) as a colorless amorphous substance.

NMR (Intermediate product 27-2)
$^1$H-NMR(CDCl$_3$) δ: 7.53–7.25 (10H, m, aromatic), 5.91 (1H, d, J=7.33 Hz, NH), 5.64 (1H, brs, NH), 5.46 (1H, d, J=7.81 Hz, NH), 5.10 (2H, s, COOCH$_2$), 4.95 (1H, d, J=3.90 Hz, H-1), 4.35 (1H, m), 4.28 (1H, m), 3.73 (3H, s, OCH$_3$), 3.72 (4H, m, (CH$_2$)$_2$O), 3.21 (2H, m, CONHCH$_2$), 2.61–2.45 (6H, m, CH$_2$N(CH$_2$)$_2$), 2.10 (4H, m, COCH$_2$), 1.83 (1H, m, CH$_2$), 1.68 (1H, m, CH$_2$), 1.59 (2H, m, CH$_2$), 1.50 (4H, m, CH$_2$), 1.36 (2H, m, CH$_2$), 1.24 (8H, m, CH$_2$)

NMR (Target compound in Example 27)
$^1$H-NMR(CD$_3$OD) δ: 7.43 (2H, d, J=7.33 Hz, aromatic), 7.33 (2H, m, aromatic), 7.25 (1H, m, aromatic), 4.94 (1H, d, J=2.93 Hz, H-1), 4.61 (1H, m, NH$_2$—CH—CO), 4.06–3.90 (4H, m), 3.81–3.74 (2H, m), 3.57–3.46 (3H, m), 3.31–3.16 (4H, m), 2.22–2.13 (4H, m, COCH$_2$), 2.02–1.86 (2H, m, NH$_2$CHCH$_2$), 1.61–1.41 (6H, m, COCH$_2$CH$_2$, CONHCH$_2$CH$_2$), 1.37–1.21 (8H, m, CH$_2$), 1.08 (2H, m, CH$_2$)
$^{13}$C-NMR(CD$_3$OD) δ: 177.3, 176.6, 171.8, 142.5, 129.3, 128.7, 127.3, 73.8, 64.8, 61.1, 58.4, 54.8, 53.9, 53.0, 51.2, 40.0, 37.1, 31.2, 30.3, 30.2, 30.1, 30.0, 29.9, 27.1, 26.5, 23.4

Example 28

Synthesis of (1S,2S)-2-(9-sialylnonanoyl)amino-3-morpholino-1-phenyl-1-propanol 9-(1-Methoxy-4,5,7,8,9-pentaacetylsialyl)nonanoic acid (976.4 mg, 1.508 mmol), methylene chloride (15 ml) and EDC (348.4 mg, 1.817 mmol) were added to (1S,2S)-2-amino-3-morpholino-1-phenyl-1-propanol (358.0 mg, 1.517 mmol), followed by stirring for 17 hours. Then, the solvent was evaporated under reduced pressure and ethyl acetate (100 ml) was added to the residue. After washed with a saturated sodium hydrogen carbonate solution (40 ml), water (40 ml) and saturated brine (40 ml) successively, the organic layer was dried over sodium sulfate and filtered, and the solvent was evaporated under reduced pressure. The resulting crude product was purified by silica gel column chromatography (chloroform:methanol=20:1) to obtain an intermediary product 28-1. Then, methanol (5 ml), tetrahydrofuran (5 ml) and sodium methoxide (112.4 mg, 2.081 mmol) were added to Intermediate product (28-1) (1.00 g, 1.155 mmol), and the mixture was stirred at room temperature for 3.5 hours. Thereafter, water (40 μl, 2.22 mmol) and 4 N sodium hydroxide (1156 μl, 4.62 mmol) was added thereto, followed by stirring for a night. Finally, the solvent was evaporated under reduced pressure and the resulting crude product was purified by gel filtration chromatography (Sephadex LH-20 (manufactured by Amersham Pharmacia Biotech), chloroform:methanol=2:1) to obtain the title compound (759.4 mg) as a colorless amorphous substance.

NMR (Intermediate product 28-1)
$^1$H-NMR(CDCl$_3$) δ: 7.37–7.26 (5H, m, aromatic), 5.87 (1H, d, J=7.33 Hz, NH), 5.41–5.37 (1H, m), 5.34 and 5.32 (1H, m), 5.18 (1H, d, J=8.79 Hz), 4.97 (1H, d, J=3.90 Hz, H-1), 4.84 (1H, m), 4.32–4.26 (2H, m), 4.12–4.02 (3H, m), 3.79 (3H, s, O—CH$_3$), 3.73 (4H, m, (CH$_2$)$_2$O), 3.20 (1H, m), 2.62–2.48 (7H, m, N(CH$_2$)$_3$, H-3'eq), 2.14, 2.13, 2.04, 2.02 (3HX4, sx4, OCOCH$_3$ or NHCOCH$_3$), 2.1 (2H, m, COCH$_2$), 1.95 (1H, t, J=12.2 Hz, H-3'ax), 1.88 (3H, s, NHCOCH$_3$ or OCOCH$_3$), 1.51 (4H, m, CH 2(CH$_2$)$_4$CH$_2$), 1.25 (8H, m, CH$_2$(CH$_2$)$_4$CH$_2$)
$^{13}$C-NMR(CDCl$_3$) δ: 173.6, 171.0, 170.7, 170.2, 170.1, 170.0, 168.5, 140.9, 128.4, 127.6, 126.0, 98.7, 76.5, 75.5, 72.4, 69.2, 69.1, 68.6, 67.4, 66.9, 65.0, 62.4, 62.3, 62.2, 59.8, 54.4, 52.6, 51.1, 49.5, 38.1, 36.7, 29.5, 29.2, 29.1, 29.0, 25.8, 25.6, 23.2, 21.1, 20.8

NMR (Target compound in Example 28)
$^1$H-NMR(CDCl$_3$:CD$_3$OD=1:1) δ: 7.35–7.20 (5H, m, aromatic), 4.90 (1H, d, J=2.93 Hz, H-1), 4.28 (1H, m, H-2), 3.90–3.43 (13H, m), 2.84 (1H, dd, J=4.2, 12.2 Hz, H-3'eq), 2.62–2.42 (6H, m, N(CH$_2$)$_3$), 2.11 (2H, m, COCH$_2$), 2.02 (3H, s, NHCOCH$_3$), 1.62–1.41 (4H, m, CH$_2$(CH$_2$)$_4$CH$_2$), 1.59 (1H, t, J=12.2 Hz, H-3'ax), 1.37–1.22 (8H, m, CH$_2$(CH$_2$)$_4$CH$_2$)
$^{13}$C-NMR(CDCl$_3$:CD$_3$OD=1:1) δ: 175.9, 175.4, 174.3, 143.3, 128.9, 128.1, 127.1, 101.7, 79.3, 78.9, 78.6, 74.1, 73.9, 70.2, 69.3, 67.8, 65.1, 60.6, 54.9, 54.0, 42.6, 37.0, 30.8, 30.3, 30.2, 29.9, 27.0, 26.8, 22.6

Activity in vitro

Test Example 1

Measurement of activity of accelerating synapse formation toward cultured neurocytes of rat fetal cerebral cortex Principle:
The activity of accelerating synapse formation was determined by measuring change of an intracellular calcium ion level resulted from the synchronized spontaneous ignition of neurocytes which is considered to show synapse activities by means of an intracellular calcium ion multipoint observation system using a calcium ion fluorescence indicator, fura-2.

Procedure
(1) Primary Culture
Primary culture of neurocytes of rat fetal cerebral cortex was carried out by modifying the method of Banker and Cowman (*Brain Res.*, 126: 397–425 (1977)). Concretely, rat fetuses at the 18th day of pregnancy were taken out from Wistar rats (available from Japan SLC), and cerebral cortices of the fetuses were taken out and cut into small pieces. After having been treated with papain (manufactured by Worthington Biochemical) at 37° C. for 30 minutes, the pieces were suspended into a Dulbecco modified Eagle's medium containing 5% bovine neonatal serum and 5% equine serum and the cortices were dissociated into single cells with Cell Striner (70 μm, Falcon). Then, the cells were inoculated into a flexiperm plate coated with 0.5% polyethyleneimine (1.0×10$^6$ cells/500 μl/well), and was cultured in 7% CO$_2$ incubator at 37° C. The medium was exchanged on 2nd, 5th, and 8th days after the culture had been started. The activity of the compound of the present invention was measured using the primary culture. The compound was added at the time when the medium was exchanged and the concentration of the compound was maintained to be 20 μM. Assay was carried out on 10th day after the culture had been started.

(2) Measurement of Activity of Accelerating Synapse Formation
The activity of accelerating synapse formation was measured according to the method of Kudo et al. (*Br. J. Pharmacol.*, 89: 191–198 (1986)). Concretely, after the medium of each well where cells were cultured was substituted with basic salt solution (BSS), 3 μl of a DMSO solution (1 mg/ml) of a calcium ion fluorescence indicator fura-2 was added, and the whole was kept at 37° C. for 1 hour. Then, after each well was washed with BSS several times, change of an intracellular calcium ion level was observed in a BSS-containing state at 37° C. by use of an intracellular calcium ion monitoring apparatus.

Result
The values on the compounds of the present invention and a control (a group where no test compound was added) are shown as relative values obtained by calculation on the basis that the value on L-PDMP is regarded as 100 in Table 2 below, wherein each Compound No. corresponds Example No.

TABLE 2

| Compound No. | Activity of synapse formation |
| --- | --- |
| Control (not added) | 83.3 |
| L-PDMP | 100.0 |
| 5 | 92.5 |
| 6 | 87.5 |
| 10 | 91.7 |
| 11 | 93.3 |
| 12 | 80.0 |
| 13 | 95.0 |
| 14 | 94.2 |
| 15 | 90.0 |
| 17 | 90.0 |
| 19 | 90.8 |
| 21 | 97.5 |
| 22 | 88.3 |
| 23 | 85.8 |
| 26 | 95.0 |
| 27 | 100.0 |
| 28 | 95.8 |

Test Example 2

Measurement of activity of enzyme for ganglioside GM3 synthesis

Principle:
The gangliosides produced by mouse B16 melanoma cell are almost composed of ganglioside GM3. Therefore, the activity of the enzyme for ganglioside GM3 synthesis can be determined conveniently by measuring the amount of $^{14}$C-Gal incorporated in a total lipid-extracted fraction through a liquid layer partition method.

Procedure
A liquid where the cells of mouse B16 melanoma were suspended was prepared with Dulbecco modified Eagle's medium containing 10% bovine fetal serum, inoculated into a 12-well plate in an amount of $2.0\times10^5$ cells/ml/well, and cultured in 5% $CO_2$ incubator at 37° C. The treatment with a test compound (24 μM) and the addition of $^{14}$C-Gal (22.2 kBq/11.7 nmol/6 μl/well) were started through the exchange of total amount of the medium 24 hours after the culture was started. Twenty-four hours after the treatment with the test compound was started, the culture mixture was treated with PBS containing 0.02% EDTA and PBS containing 0.25% trypsin successively to recover the cells.

Then, a mixed solvent of chloroform:methanol=2:1 (3 ml) was added to the cell pellet and, after the subjection to an ultrasonication for 30 minutes, the supernatant was recovered. Furthermore, a mixed solvent of chloroform:methanol=1:1 (3 ml) was added to the residual pellet after the recovery of the supernatant, and a similar operation was carried out. The resulting supernatant was combined with the first supernatant and the whole was evaporated to dryness under a nitrogen stream. A desalinated water (1.0 ml) was added to the total lipid-extracted fraction. After having been subjected to an ultrasonication for 1 minute, the mixture was transferred into a dialysis tube and dialyzed against water for 2 days. The sample after the dialysis was transferred into a vial for liquid scintillation counter and, after the addition of scintillator, the activity of incorporating $^{14}$C-Gal was measured on scintillation counter.

Result

The values of activity of the compounds of the present invention are shown as relative values obtained by calculation on the basis that the value of a control (a group where no test compound was added) is regarded as 100 in Table 3 below.

Test Example 3

Measurement of Synthesized Amount of Ganglioside GM3

Procedure

A liquid where the cells of mouse B16 melanoma were suspended was prepared with Dulbecco modified Eagle's medium containing 10% bovine fetal serum, inoculated into a culture flask (175 cm$^2$) in an amount of $0.8\times10^7$ cells/20 ml, and cultured in 5% $CO_2$ incubator at 37° C. The treatment with a test compound (25 μM) was started through the exchange of three fourths of the medium 24 hours after the culture was started. Twenty-four hours after the treatment with the test compound was started, the culture mixture was treated with PBS containing 0.02% EDTA and PBS containing 0.25% trypsin successively to recover the cells.

Then, a mixed solvent of chloroform:methanol=2:1 (4 ml) was added to the cell pellet and, after the subjection to an ultrasonication for 30 minutes, the cell pellet solution was allowed to stand at room temperature for a night and the supernatant was recovered. Furthermore, a mixed solvent of chloroform:methanol=1:1 (4 ml) was added to the residual pellet after the recovery of the supernatant, and a similar operation was carried out. The resulting supernatant was combined with the first supernatant and the whole was evaporated to dryness under a nitrogen stream. To the total lipid fraction was added a 0.1 N methanolic sodium hydroxide solution (2.0 ml) and the mixture was allowed to stand at 40° C. for 2 hours. Thereafter, 1 N hydrochloric acid (0.2 ml) was added thereto and the mixture was allowed to stand for 1.5 hours.

Then, the mixture was washed with n-hexane (2 ml×2) and, after the lower layer thus washed was evaporated to dryness under a nitrogen stream, the residue was desalinated by gel filtration chromatography (Sephadex LH-20 (manufactured by Amersham Pharmacia Biotech), diameter of 10 mm, height of 120 mm) using chloroform:methanol= 2:1 as the eluting solvent. After the desalinated eluate fraction was evaporated to dryness under a nitrogen stream, the residue was applied onto an anion-exchange resin column (DEAE-Sephadex, diameter of 10 mm, height of 40 mm) equilibrated with chloroform:methanol:water=30:60:8 using chloroform:methanol:1M sodium acetate solution= 30:60:8 as the eluting solvent to obtain an acidic lipid fraction. Then, the acidic lipid fraction was desalinated by means of the resin column in a similar manner, and then subjected to HPTLC (length of 200 mm×breadth of 100 mm, developing solvent; chloroform:methanol:water=60:35:8). After orcinol-sulfuric acid reagent had been sprayed on the plate, it was heated at 110° C. for 5 minutes and colored spot of ganglioside GM3 was quantitatively determined by means of densitometer (a measuring wavelength of 505 nm).

Result

The values on the compounds of the present invention are shown as relative values obtained by calculation on the basis that the value of a control (a group where no test compound was added) is regarded as 100 in Table 3 below.

TABLE 3

|  | Activity of accelerating glycolipid biosynthesis (Test Example 2) | Glycolipid content (Test Example 3) |
| --- | --- | --- |
| Control | 100 | 100 |
| L-PDMP | 95.2 | 100.7 |
| 1 | 85.2 | — |
| 2 | 130.9 | — |
| 3 | 98.6 | — |
| 4 | 71.3 | — |
| 5 | 122.3 | 131.2 |
| 25 | 89.2 | 114.5 |

Based on the above results, it was evidenced that the compounds of the present invention have a high activity of synapse formation as compared with the control. Furthermore, it is confirmed that some of the compounds of the present invention are excellent in the activity of accelerating glycolipid biosynthesis as compared with L-PDMP.

Safety

Test Example 4

Safety Test by Intravenous Single Administration to Mouse

The safety of the compounds of the present invention in the examples and L-PDMP was examined using 6 week old Crj mice. Concretely, the test was carried out at a concentration of the test medicament of 20 mg/ml using physiological saline containing 5.0% Tween 80 as the medica ment carrier. The medicament solution prepared under the above conditions was administrated from the caudal vein at an injection rate of 1 ml/minute in an amount of 200 mg/kg, and the general state was observed.

As a result, it was confirmed that the compounds of the present invention are safer than L-PDMP.

Activity in vivo

Test Example 5

Comparison of Tissue Distribution of Compound in Example 19 with L-PDMP

Procedure

Tissue distribution of the compound in Example 19 was compared with that of L-PDMP using 6–8 week old Wistar male rats.

As oral administration, a physiological saline containing 20 mg/ml of a test substance was administered at 100 mg/5 ml/kg, and as intravenous administration, a physiological saline containing 1.25 mg/ml of a test substance was administered to the cervical vein at 5 mg/4 ml/kg.

After the predetermined time had passed since the above administration, blood was collected from the rat cervical vein, a 3.8% sodium citrate solution was added thereto at ¹⁄₁₀ volume, followed by centrifugation at 3,000 rpm for 15 minutes to obtain the supernatant as a plasma sample.

Also, after the predetermined time had passed since the above administration, the skeletal muscle was collected from the femoral region of both hind legs, ice water was added thereto at 4 ml/g tissue, followed by homogenization, and the same volume of acetonitrile was added thereto, followed by vigorously stirring and centrifugation at 4000 rpm for 10 minutes to obtain the supernatant as a skeletal muscle sample.

The plasma and skeletal muscle samples were extracted by OASIS HLB solid phase extraction column (manufactured by Waters), and the concentration of the test compound in the plasma and the muscle was determined by high performance liquid chromatography (HPLC). The conditions of HPLC analysis were as follows:

Detection wavelength: 218 nm
Column: DAISO PACK SP-120-5-ODS-BP
Column temperature: 40° C.
Mobile phase: 0.1% trifluoroacetic acid solution:methanol= 36:64 (for L-PDMP); 0.1% trifluoroacetic acid solution:methanol=48:52 (for the compound in Example 19)
Flow rate: 1.0 ml/min Result The concentrations in the plasma and skeletal muscle of the compound in Example 19 and L-PDMP after the predetermined time has been passed since the administration of the test compounds are shown in Tables 4–6 below. The values are the mean values of at least two test samples. Specifically, Table 4, Table 5, and Table 6 show the concentrations in the plasma after the oral administration of 100 mg/kg, the concentrations in the skeletal muscle after the oral administration of 100 mg/kg, and the concentrations in the plasma after the intravenous administration of 5 mg/kg, respectively.

TABLE 4

| Time (min) | 5 | 15 | 30 | 60 |
|---|---|---|---|---|
| L-PDMP | 0.01 | 1.36 | 2.10 | 1.44 |
| Compound in Ex. 19 | 2.62 | 8.66 | 6.14 | 0.95 |

Unit: μg/ml plasma

TABLE 5

| Time (min) | 5 | 15 | 30 |
|---|---|---|---|
| L-PDMP | ND | 3.37 | 5.81 |
| Compound in Ex. 19 | 2.73 | 6.91 | 6.38 |

Unit: μg/g muscle
ND: not detected

TABLE 6

| Time (min) | 10 | 25 |
|---|---|---|
| L-PDMP | 1.03 | 0.62 |
| Compound in Ex. 19 | 2.24 | 0.56 |

Unit: μg/ml plasma

As apparent from the above results, the compound of the present invention (compound in Example 19) is kept in the plasma and skeletal muscle for a longer time and has a higher tissue distribution than L-PDMP.

This application is based on Japanese applications No. Hei. 11-346526 filed on Dec. 6, 2000, the entire content of which is incorporated hereinto by reference.

While the invention has been described in detail and with reference to specific embodiments thereof, it will be apparent to one skill in the art that various changes and modifications can be made therein without departing from the spirit and scope thereof.

What is claimed is:

1. An aminoalcohol derivative represented by formula (I):

(I)

[Chemical structure: morpholine-N-CH₂-C*H(NHR)-C*H(OH)-phenyl]

wherein * represents an asymmetric carbon; and
R represents a residue of a monocarboxylic acid derivative represented by the following (i) or (ii), or a residue of a dicarboxylic acid or a derivative thereof represented by the following (iii):
(i) a residue of glycine or polyglycine represented by $(COCH_2NH)_mZ$,
wherein m represents an integer of from 1 to 3; and Z represents an amino-protecting group or an alkanoyl group;
(ii) a residue of a carboxylic acid derivative represented by CO—W—Y,
wherein W represents an alkylene group or a cycloalkylene group; and
Y represents a hydroxyl group, a monosaccharide residue, an aryl group which is optionally substituted, or an alkoxyl group optionally having an oxygen atom in the alkyl chain;
(iii) a residue of a dicarboxylic acid or a derivative thereof represented by CO—W—CO—X, wherein W represents an alkylene group or a cycloalkylene group; and X represents a hydroxyl group, a chain or cyclic alkoxyl group, an alkyl group, an a-amino acid residue, or $NR^1R^2$, in which $R^1$ and $R^2$ are the same or different and each independently represents a hydrogen atom, a chain or cyclic alkyl group optionally having an oxygen atom in the alkyl chain, or a chain or cyclic hydroxyalkyl group optionally having an oxygen atom in the alkyl chain, or a pharmaceutically acceptable salt thereof.

2. The aminoalcohol derivative according to claim 1, wherein R is represented by any one of the following (i) to (iii) in formula (I):

(i) $(COCH_2NH)_mZ$, wherein Z represents an amino-protecting group selected from an aralkyloxycarbonyl group having from 8 to 15 carbon atoms and an alkoxycarbonyl group having from 5 to 7 carbon atoms, or an alkanoyl group having from 4 to 8 carbon atoms;

(ii) CO—W—Y, wherein W represents an alkylene group having from 1 to 12 carbon atoms or a cycloalkylene group having from 4 to 8 carbon atoms; and Y represents a hydroxyl group, a glucose residue, a galactose residue, an N-acetylglucosamine residue, an N-acetylgalactosamine residue, a mannose residue, a fucose residue, a sialic acid residue, a phenyl group which is optionally substituted, an alkoxyl group having from 1 to 6 carbon atoms, or an alkoxyl group having from 4 to 12 carbon atoms having from 1 to 3 oxygen atoms in the alkyl chain;

(iii) CO—W—CO—X, wherein W represents an alkylene group having from 1 to 12 carbon atoms or a cycloalkylene group having from 4 to 8 carbon atoms; and X represents a hydroxyl group, an alkoxyl group having from 1 to 8 carbon atoms, a cycloalkoxyl group having from 5 to 8 carbon atoms, an alkyl group having from 1 to 6 carbon atoms, a residue of an α-amino acid having a reactive functional group in the side chain, or $NR^1R^2$, in which $R^1$ and $R^2$ are the same or different and each independently represents a hydrogen atom, an alkyl group having from 1 to 6 carbon atoms, cyclohexyl group or a hydroxyalkyl group having from 2 to 4 carbon atoms, or a pharmaceutically acceptable salt thereof.

3. The aminoalcohol derivative according to claim 1, wherein R is represented by any one of the following (i) to (iii) in formula (I):

(i) $(COCH_2NH)_mZ$, wherein Z represents a benzyloxycarbonyl group, a t-butoxycarbonyl group, or a hexanoyl group;

(ii) CO—W—Y, wherein W represents an alkylene group having from 1 to 9 carbon atoms; and Y represents a hydroxyl group, a glucose residue, a galactose residue, an N-acetylglucosamine residue, an N-acetylgalactosamine residue, a sialic acid residue, a phenyl group which is substituted with an alkoxyl group having from 1 to 3 carbon atoms, an alkoxyl group having from 1 to 4 carbon atoms, or an alkoxyl group having from 6 to 8 carbon atoms having an oxygen atom in the alkyl chain;

(iii) CO—W—CO—X, wherein W represents an alkylene group having from 2 to 8 carbon atoms or a cyclohexylene group; and X represents a hydroxyl group, an alkoxyl group having from 1 to 4 carbon atoms, a cyclohexyloxy group, a methyl group, a residue of an amino acid selected from lysine, arginine, histidine, aspartic acid, glutamic acid, ornithine, cysteine, serine, threonine and tyrosine, or $NR^1R^2$, in which $R^1$ and $R^2$ are the same or different and each independently represents a hydrogen atom, a straight chain alkyl group having from 1 to 6 carbon atoms, a cyclohexyl group, or a hydroxyethyl group, or a pharmaceutically acceptable salt thereof.

4. The aminoalcohol derivative according to claim 1, wherein, in formula (I), R is represented by CO—W—CO—X, in which W represents an alkylene group having from 2 to 8 carbon atoms; and X represents a hydroxyl group, an alkoxyl group having from 1 to 4 carbon atoms, or a methyl group, or a pharmaceutically acceptable salt thereof.

5. The aminoalcohol derivative according to claim 1, wherein, in formula (I), R is represented by CO—W—CO—X, in which W represents an alkylene group having from 4 to 8 carbon atoms; and X represents a lysine residue or an ornithine residue, or a pharmaceutically acceptable salt thereof.

6. The aminoalcohol derivative according to claim 1, wherein, in formula (I), R is represented by CO—W—CO—X, in which W represents an alkylene group having from 4 to 8 carbon atoms or cyclohexylene group; and X represents $NR^1R^2$, in which $R^1$ and $R^2$ are the same or different and each independently represents a hydrogen atom, a methyl group, an ethyl group, a propyl group, an n-butyl group, an n-hexyl group, a cyclohexyl group, or a hydroxyethyl group, or a pharmaceutically acceptable salt thereof.

7. The aminoalcohol derivative according to claim 1, wherein, in formula (I), R is represented by CO—W—Y, in which W represents a nonylene group; and Y represents a hydroxyl group, or a pharmaceutically acceptable salt thereof.

8. The aminoalcohol derivative according to claim 1, wherein, in formula (I), R is represented by CO—W—Y, in which W represents a methylene group; and Y represents an n-butoxy group or an alkoxyl group having from 6 to 8 carbon atoms having an oxygen atom in the alkyl chain, or a pharmaceutically acceptable salt thereof.

9. The aminoalcohol derivative according to claim 1, wherein, in formula (I), R is represented by CO—W—Y, in which W represents an octylene group; and Y represents a sialic acid residue, or a pharmaceutically acceptable salt thereof.

10. A medicament comprising, as an active ingredient, the aminoalcohol derivative or pharmaceutically acceptable salt thereof according to claim 1.

11. The medicament according to claim 10, comprising, as an active ingredient, the aminoalcohol derivative wherein R is represented by (i) in formula (I), or pharmaceutically acceptable salt thereof.

12. The medicament according to claim 10, comprising, as an active ingredient, the aminoalcohol derivative wherein R is represented by (ii) in formula (I), or pharmaceutically acceptable salt thereof.

13. The medicament according to claim 10, comprising, as an active ingredient, the aminoalcohol derivative wherein R is represented by (iii) in formula (I), or pharmaceutically acceptable salt thereof.

14. The medicament according to claim 10, which is an agent for treating neuronal diseases.

15. The medicament according to claim 10, which is an agent for protecting brain.

* * * * *